US009655653B2

(12) United States Patent
Lindner et al.

(10) Patent No.: US 9,655,653 B2
(45) Date of Patent: May 23, 2017

(54) VERTEBRAL COLUMN-STABILIZING SYSTEM AND SURGICAL FASTENING ELEMENT FOR A VERTEBRAL COLUMN-STABILIZING SYSTEM

(71) Applicant: Aesculap AG, Tuttlingen (DE)

(72) Inventors: Stephan Lindner, Wurmlingen (DE); Sven Krüger, Trossingen (DE)

(73) Assignee: Aesculap AG (DE)

( * ) Notice: Subject to any disclaimer, the term of this patent is extended or adjusted under 35 U.S.C. 154(b) by 0 days.

(21) Appl. No.: 14/827,479

(22) Filed: Aug. 17, 2015

(65) Prior Publication Data

US 2015/0351810 A1    Dec. 10, 2015

Related U.S. Application Data

(63) Continuation of application No. PCT/EP2014/055468, filed on Mar. 19, 2014.

(30) Foreign Application Priority Data

Mar. 22, 2013 (DE) .......................... 10 2013 102 976
Jul. 15, 2013 (DE) .......................... 10 2013 107 498

(51) Int. Cl.
*A61B 17/70* (2006.01)
*A61B 90/00* (2016.01)

(52) U.S. Cl.
CPC ...... *A61B 17/7032* (2013.01); *A61B 17/7037* (2013.01); *A61B 17/7086* (2013.01); *A61B 17/7091* (2013.01); *A61B 2090/037* (2016.02)

(58) Field of Classification Search
CPC .................................. A61B 17/7083–17/7091

USPC ........................................................ 606/86 A
See application file for complete search history.

(56) References Cited

U.S. PATENT DOCUMENTS

| 5,667,508 A | 9/1997 | Errico |
| 6,139,549 A | 10/2000 | Keller |
| 6,280,445 B1 * | 8/2001 | Morrison ........... A61B 17/7007 606/280 |
| 6,440,132 B1 * | 8/2002 | Jackson ............. A61B 17/7032 606/267 |
| 7,985,242 B2 | 7/2011 | Forton |

(Continued)

FOREIGN PATENT DOCUMENTS

| DE | 9403231 | 4/1994 |
| DE | 29606468 | 8/1997 |

(Continued)

OTHER PUBLICATIONS

International Search Report for International Application No. PCT/EP2014/055468 mailed Jun. 16, 2014.

*Primary Examiner* — Nicholas Plionis
(74) *Attorney, Agent, or Firm* — RatnerPrestia

(57) ABSTRACT

A surgical fastening element for a spinal column stabilization system includes at least two fastening elements and at least one connecting element, the surgical fastening element including a fastening section, a holding section with a connecting element receptacle, and a fixing element fixable on the holding section for fixing the connecting element in the connecting element receptacle. The fixing element carries a holding down element for holding the connecting element down in the connecting element receptacle.

20 Claims, 21 Drawing Sheets

(56) References Cited

U.S. PATENT DOCUMENTS

| | | | |
|---|---|---|---|
| 2002/0161368 A1* | 10/2002 | Foley | A61B 17/1671 128/898 |
| 2004/0039383 A1* | 2/2004 | Jackson | A61B 17/7091 606/270 |
| 2005/0240180 A1 | 10/2005 | Vienney | |
| 2006/0149241 A1 | 7/2006 | Richelsoph | |
| 2008/0086132 A1* | 4/2008 | Biedermann | A61B 17/7037 606/279 |
| 2009/0062865 A1 | 3/2009 | Schumacher | |
| 2009/0240292 A1* | 9/2009 | Butler | A61B 17/7085 606/86 A |
| 2010/0262195 A1* | 10/2010 | Jackson | A61B 17/7032 606/305 |
| 2010/0331897 A1 | 12/2010 | Lindner | |
| 2011/0040335 A1* | 2/2011 | Stihl | A61B 17/7032 606/302 |

FOREIGN PATENT DOCUMENTS

| | | |
|---|---|---|
| EP | 1891904 | 2/2008 |
| EP | 2266483 | 12/2010 |
| FR | 2624720 | 6/1989 |
| FR | 2829014 | 3/2003 |
| WO | 9621396 | 7/1996 |
| WO | 2009132110 | 10/2009 |

* cited by examiner

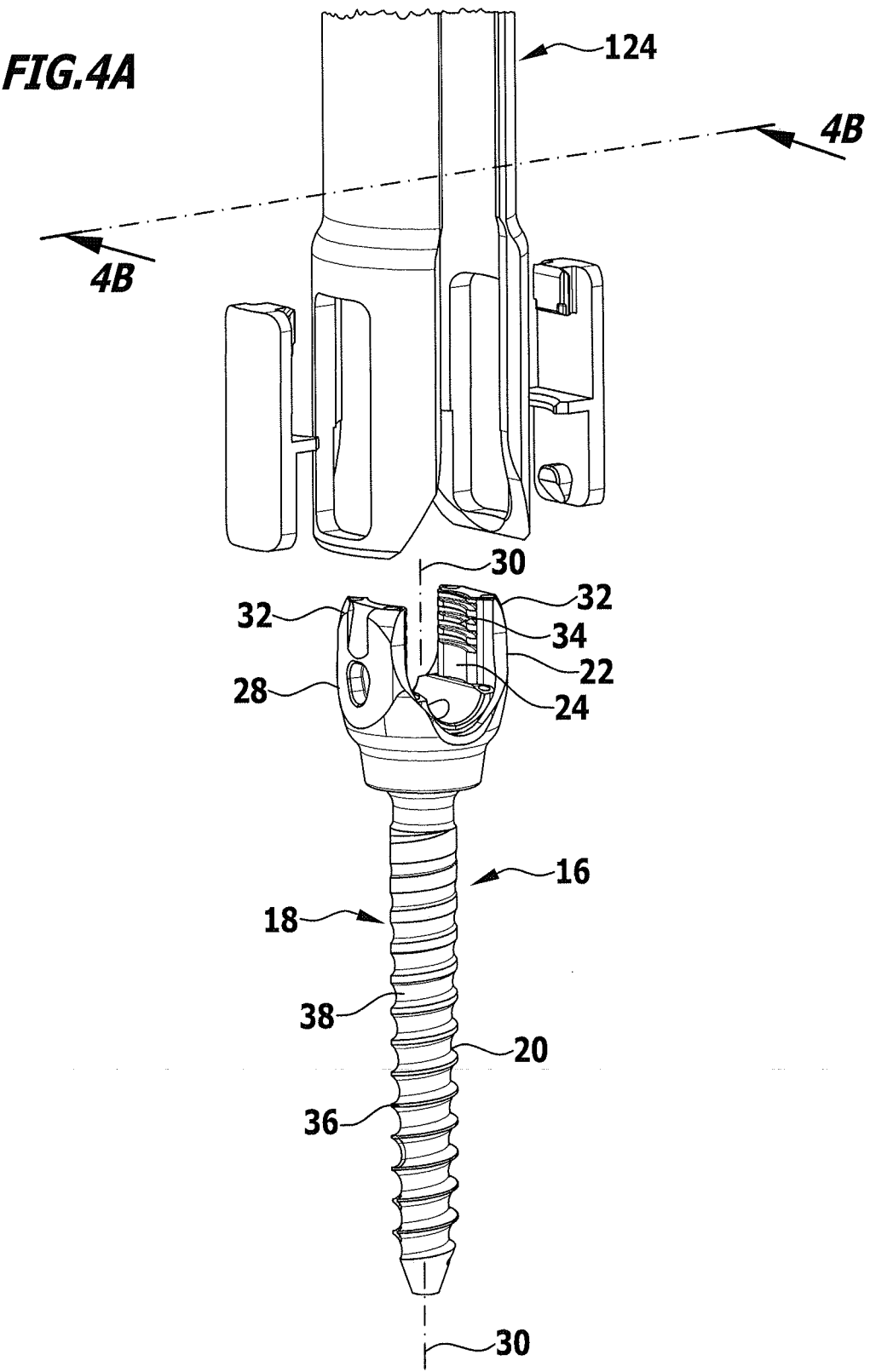

*FIG.4B*                *FIG.4C*
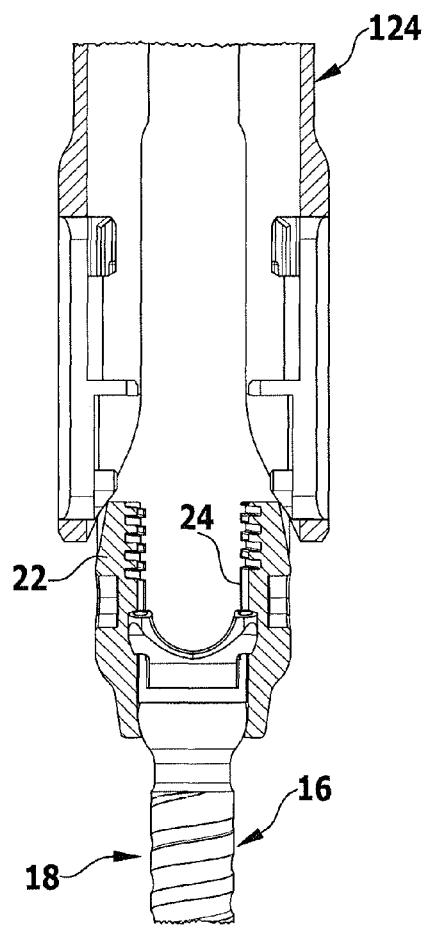
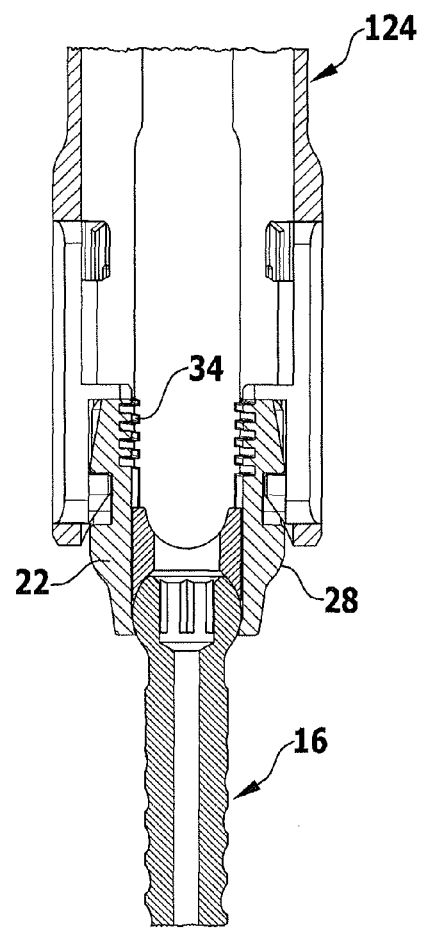

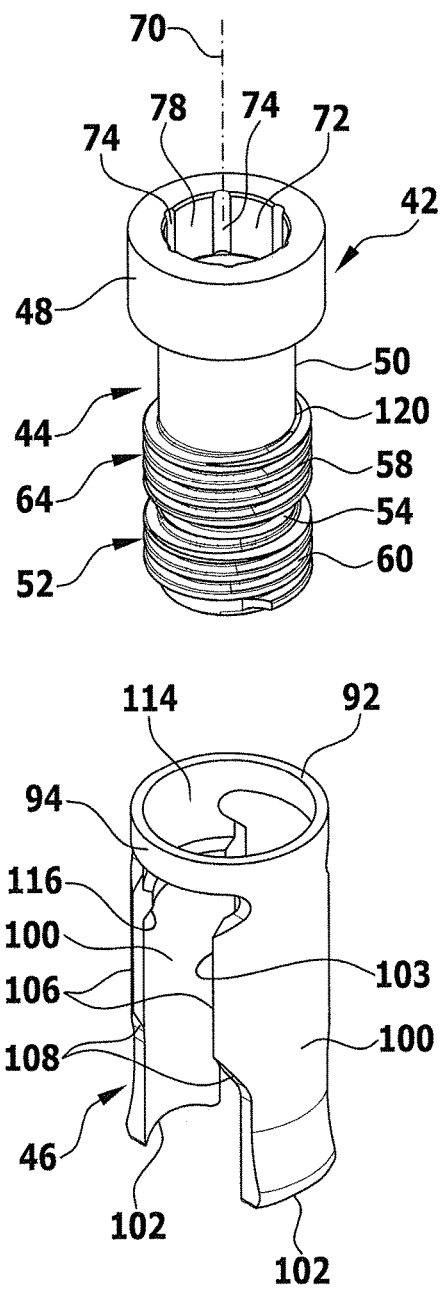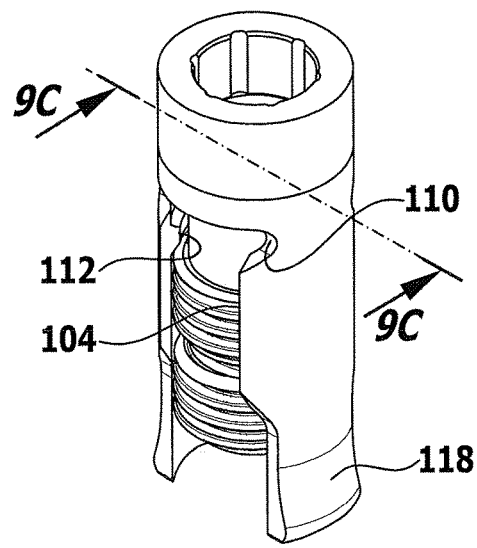
FIG.9A
FIG.9B

VERTEBRAL COLUMN-STABILIZING SYSTEM AND SURGICAL FASTENING ELEMENT FOR A VERTEBRAL COLUMN-STABILIZING SYSTEM

CROSS-REFERENCE TO RELATED APPLICATIONS

This application is a continuation of international application number PCT/EP2014/055468 filed on Mar. 19, 2014 and claims the benefit of German application number 10 2013 102 976.0 filed on Mar. 22, 2013 and of German application number 10 2013 107 498.7 filed on Jul. 15, 2013.

The present disclosure relates to the subject matter disclosed in international application number PCT/EP2014/055468 filed on Mar. 19, 2014, German application number 10 2013 102 976.0 filed on Mar. 22, 2013 and German application number 10 2013 107 498.7 filed on Jul. 15, 2013, all of which are incorporated herein by reference in their entirety and for all purposes.

FIELD OF THE INVENTION

The present invention relates to surgical fastening elements for spinal column stabilization systems generally, and more specifically to a surgical fastening element for a spinal column stabilization system comprising at least two fastening elements and at least one connecting element, the surgical fastening element comprising a fastening section, a holding section with a connecting element receptacle, and a fixing element fixable on the holding section for fixing the connecting element in the connecting element receptacle.

The present invention further relates to spinal column stabilization systems generally, and more specifically to a spinal column stabilization system comprising at least two surgical fastening elements and at least one connecting element, at least one of the at least two surgical fastening elements comprising a fastening section, a holding section with a connecting element receptacle, and a fixing element fixable on the holding section for fixing the connecting element in the connecting element receptacle.

BACKGROUND OF THE INVENTION

Surgical fastening elements and spinal column stabilization systems of the kind described at the outset are known, for example, from EP 2 266 483 A1. The known fastening elements, which, in particular, may be in the form of fastening screws, for example, pedicle screws, are inserted into adjacent vertebral bodies and connected to one another by one or more connecting elements, in order to stabilize the spinal column. The connecting elements may be rod-shaped and/or plate-shaped, so that a defined connection is in this way settable between adjacent vertebral bodies. The spinal column stabilization systems may, of course, also include further fastening elements and connecting elements, so that not only two, but also two, three or more movement segments of the spinal column can be coupled to one another and stabilized.

Introducing the connecting elements into the connecting element receptacle and then inserting the usually rather small fixing element is a problem, in particular, in minimally invasive implantation of such spinal column stabilization systems. For easier insertion of the fixing element, the connecting element is usually pressed into the connecting element receptacle.

In known systems, the introduction of the fastening elements and the fixing of the connecting elements consists, in principle, of several steps: introducing and anchoring the fastening element, inserting the connecting element into the connecting element receptacle, pressing the connecting element into the connecting element receptacle and then introducing the fixing element and fixing the connecting element immovably on the connecting element receptacle with the fixing element. The purpose of pressing the connecting element into the connecting element receptacle is, in particular, to bring the connecting element into a defined end position in the connecting element receptacle and hold it there so that the fixing element can be introduced and preferably fixed without force on the holding section, in order to fix the connecting element.

In particular, it is known to use external sleeves for pressing the connecting element into the connecting element receptacle. This does, however, have the disadvantage that a skin incision has to be significantly enlarged for this. Alternatively, fastening elements with elongated holding sections which, after the fixing element is fixed, may or must be partially removed, for example, by breaking off elongations on the holding section of the fixing element serving as guides, are also known. However, both variants have disadvantages which increase the effort involved in the surgery and, in particular, prolong the operating time.

SUMMARY OF THE INVENTION

In a first aspect of the invention, a surgical fastening element is provided for a spinal column stabilization system comprising at least two fastening elements and at least one connecting element. Said surgical fastening element comprises a fastening section, a holding section with a connecting element receptacle, and a fixing element fixable on the holding section for fixing the connecting element in the connecting element receptacle. The fixing element carries a holding down element for holding the connecting element down in the connecting element receptacle.

In a second aspect of the invention, a spinal column stabilization system comprises at least two surgical fastening elements and at least one connecting element. At least one of the at least two surgical fastening elements comprises a fastening section, a holding section with a connecting element receptacle, and a fixing element fixable on the holding section for fixing the connecting element in the connecting element receptacle. The fixing element carries a holding down element for holding the connecting element down in the connecting element receptacle.

BRIEF DESCRIPTION OF THE DRAWING FIGURES

The foregoing summary and the following description may be better understood in conjunction with the drawing figures, of which:

FIG. 4A shows a diagrammatic exploded representation of a distal end of the guide sleeve before engagement with the fastening element;

FIG. 4B shows a sectional view taken along line 4B-4B in FIG. 4A;

FIG. 4C shows a view in analogy with FIG. 4B, in which the guide sleeve is coupled to the fastening element;

FIG. 9A shows an exploded representation of the fixing element and the holding down element;

FIG. 9B shows a perspective view of the fixing element and the holding down element in the connected position;

DETAILED DESCRIPTION OF THE INVENTION

Figure 1:
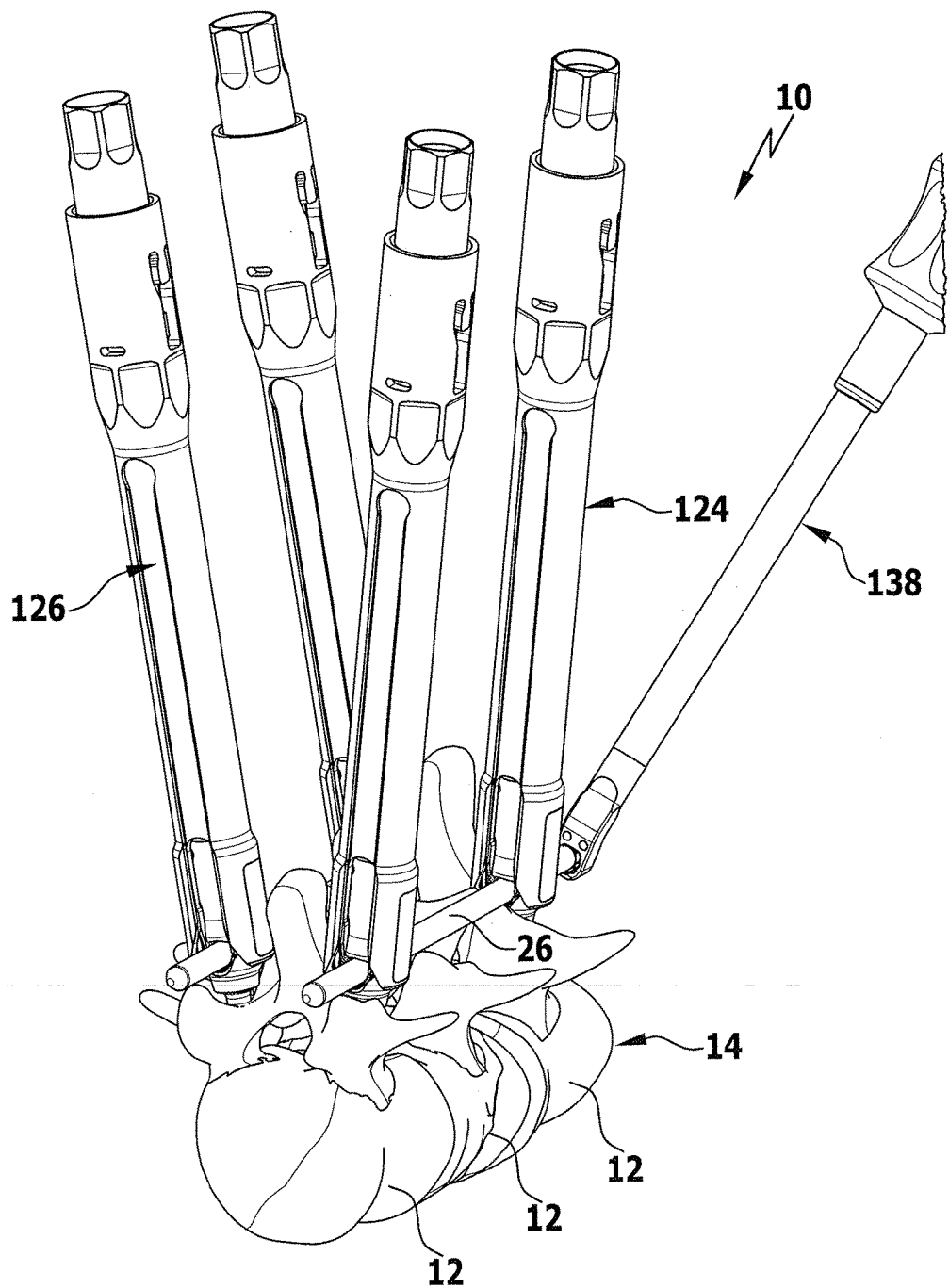
FIG. 1 shows a diagrammatic overall view of a spinal column stabilization system during implantation thereof.
Figure 2:
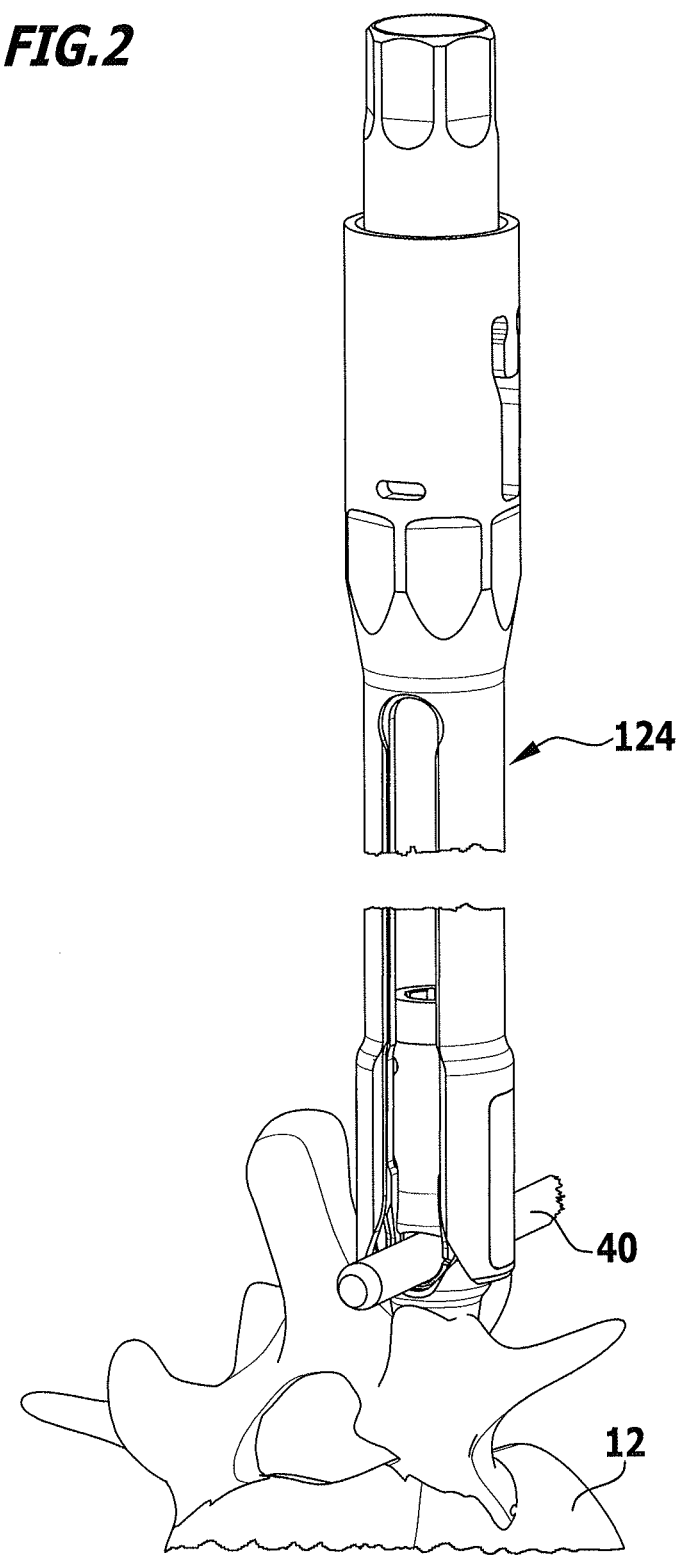
FIG. 2 shows a diagrammatic representation of a guide sleeve coupled to a fastening element inserted in a vertebral body.
Figure 3A:
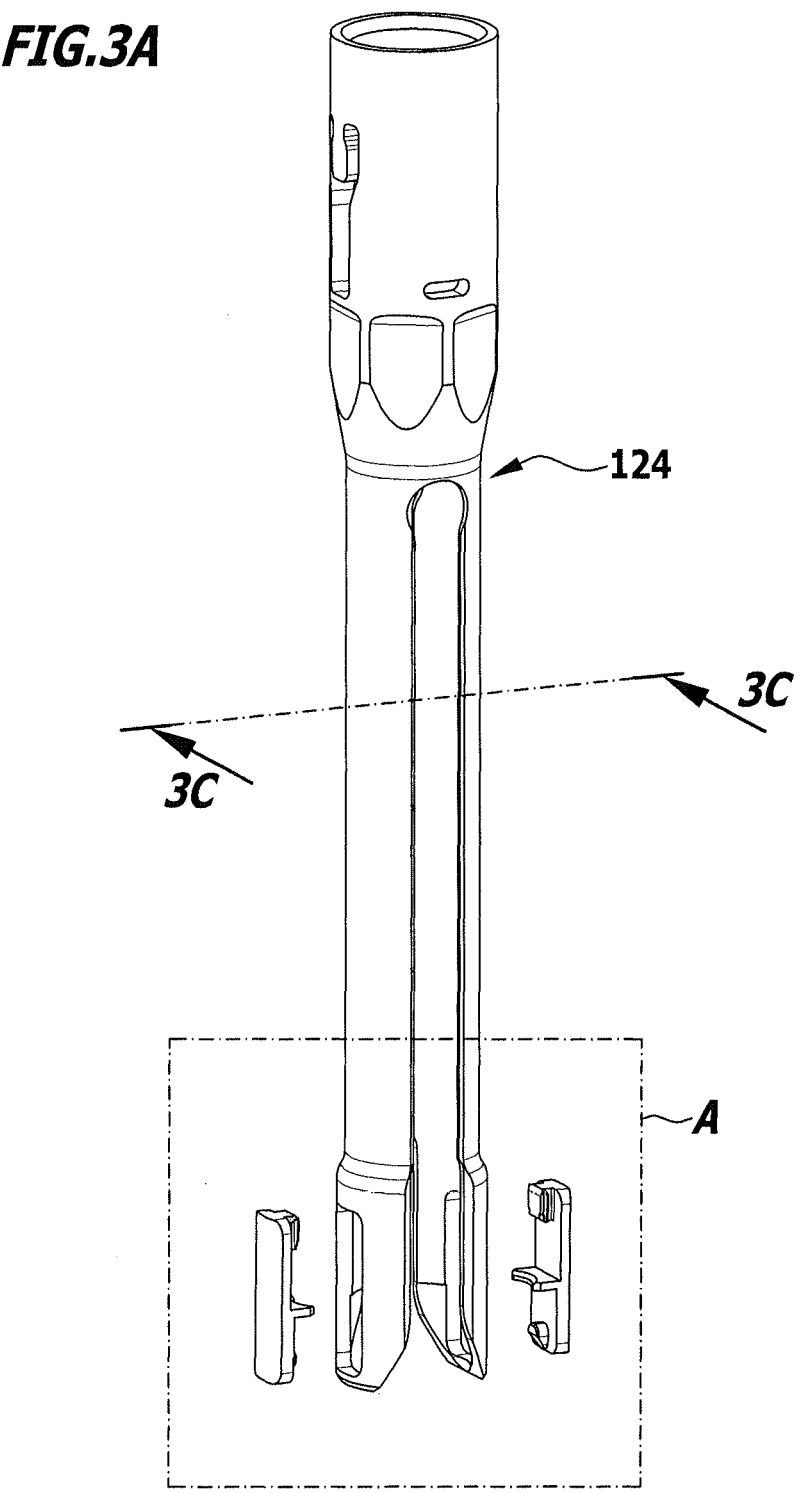
FIG. 3A shows an exploded representation of the guide sleeve.
Figure 3B:
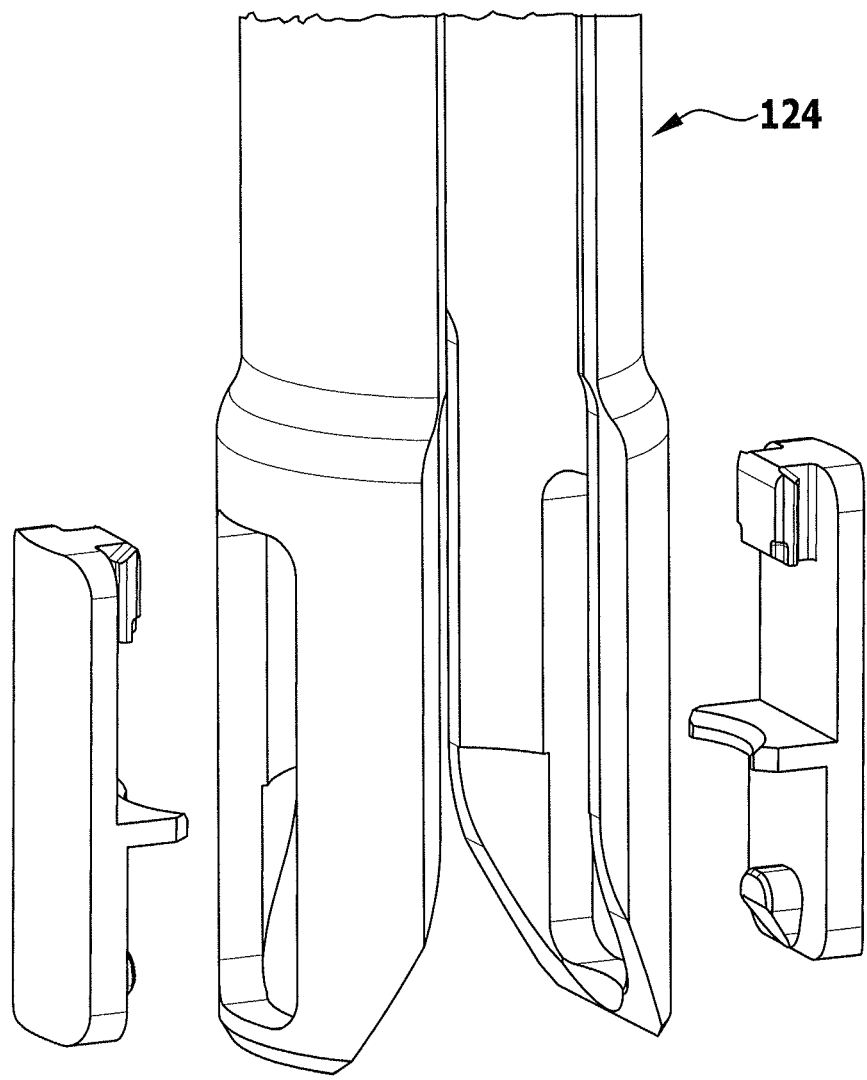
FIG. 3B shows an enlarged view of area A in FIG. 3A.
Figure 3C:
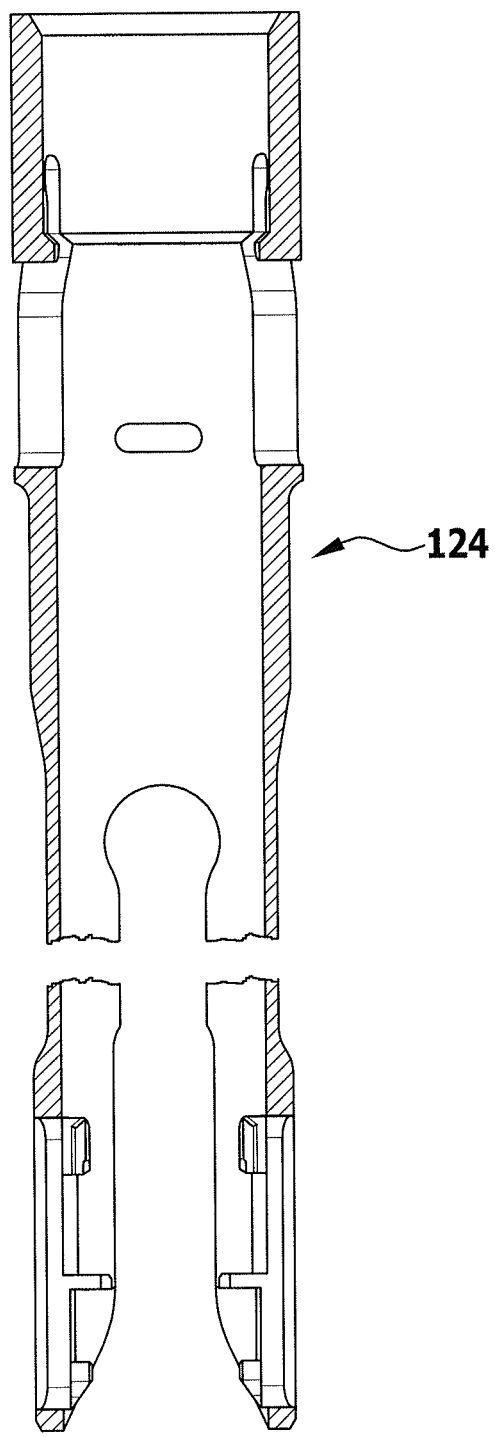
FIG. 3C shows a sectional view taken along line 3C-3C in FIG. 3A.
Figure 5A:
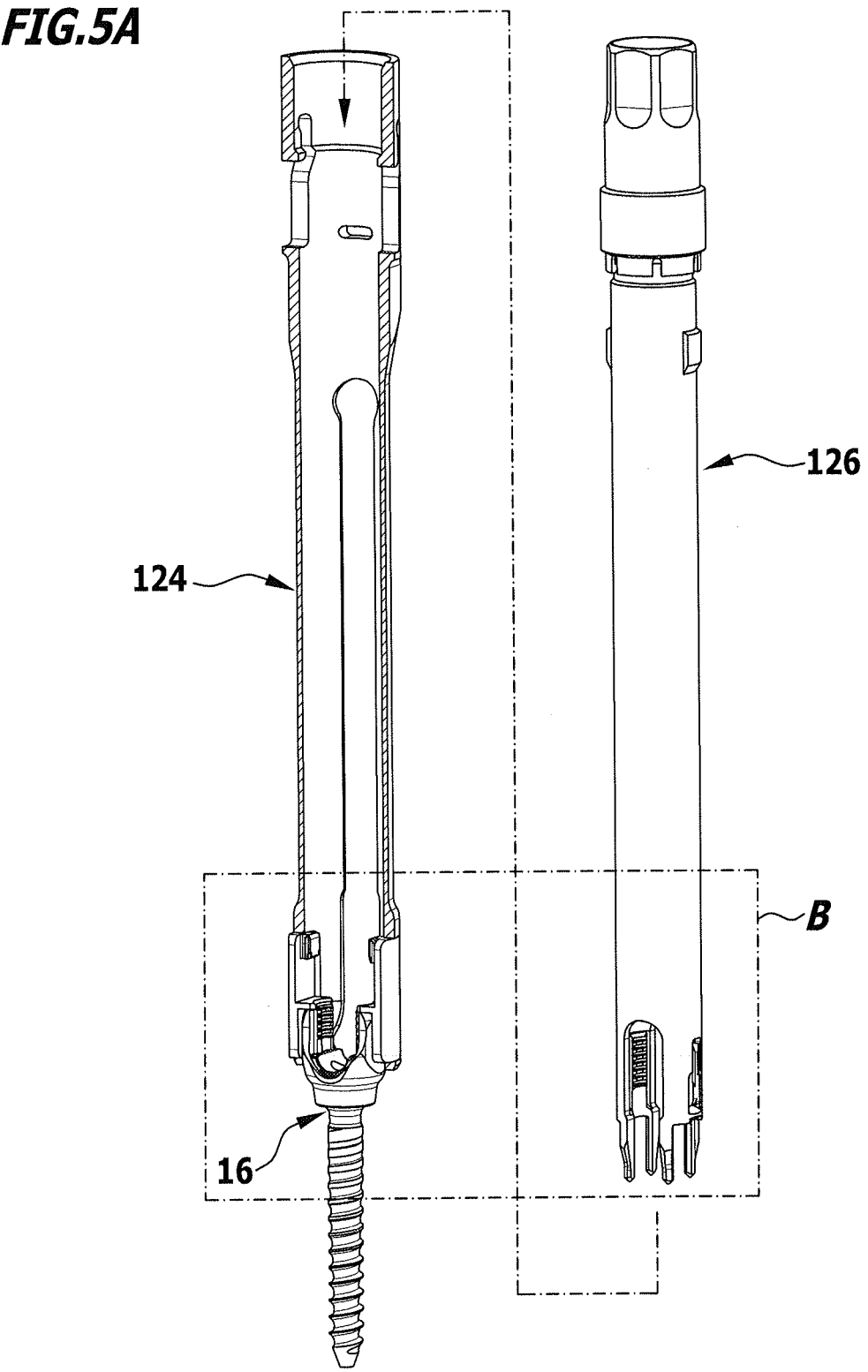
FIG. 5A shows a longitudinal sectional view of the guide sleeve coupled to the fastening element before insertion of an inner sleeve.
Figure 5B:
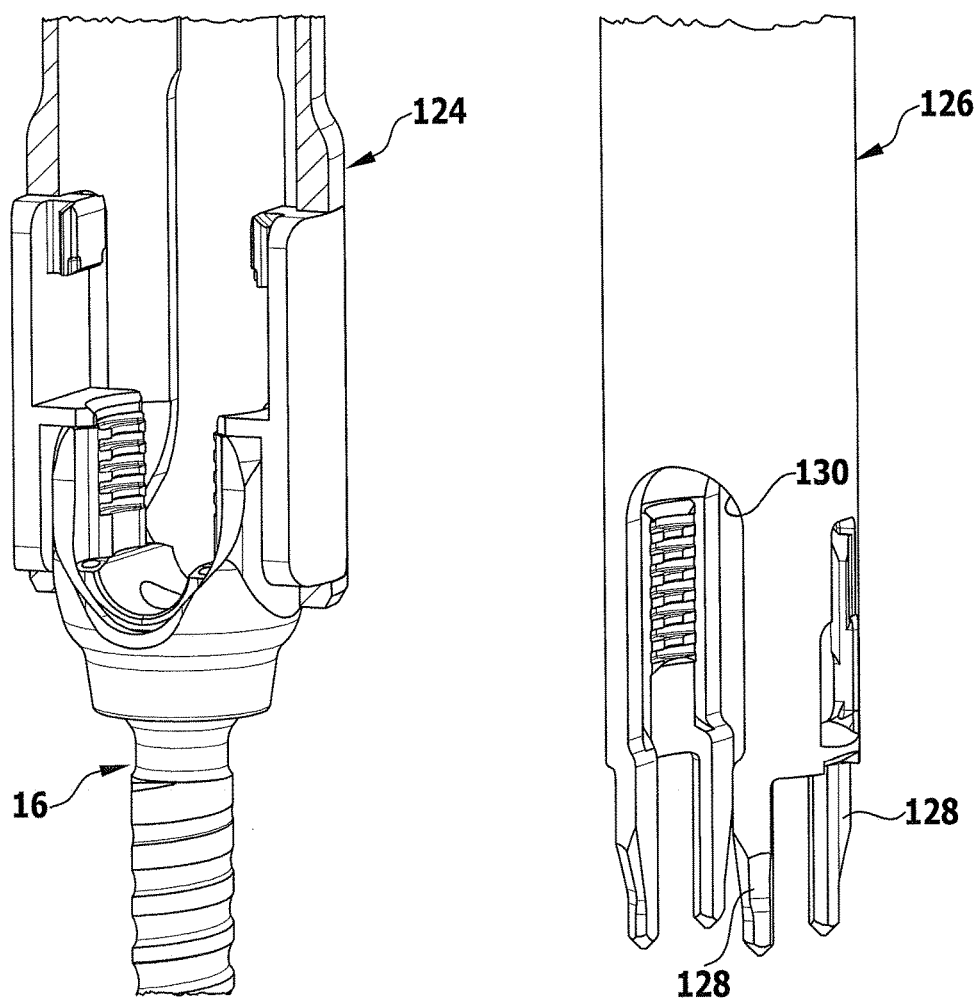
FIG. 5B shows an enlarged view of area B in FIG. 5A.
Figure 6A:
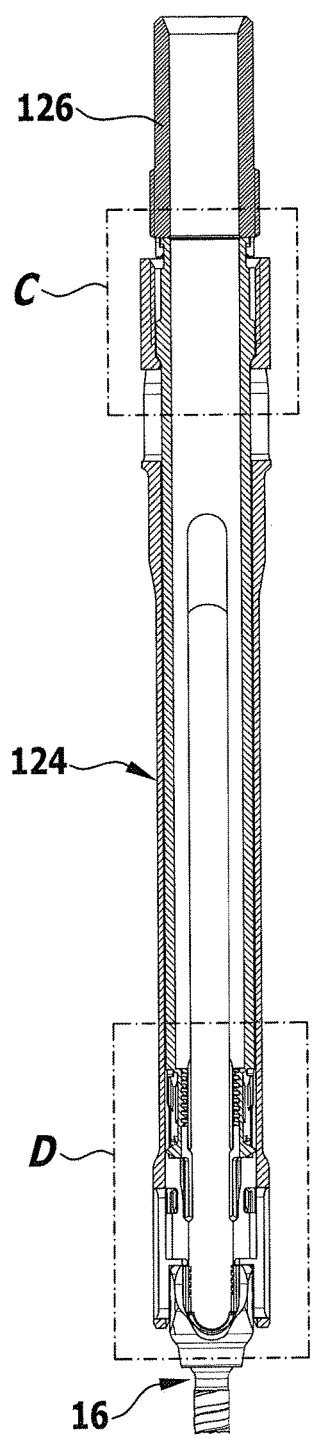
FIG. 6A shows a longitudinal sectional view of the guide sleeve coupled to the fastening element with the inner sleeve inserted.
Figure 6B:
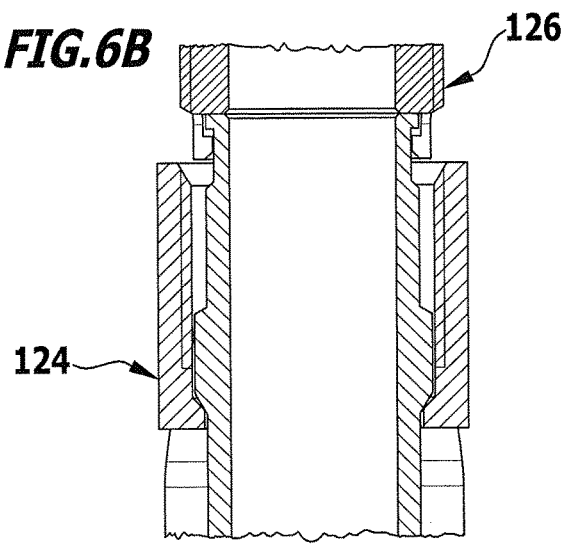
FIG. 6B shows an enlarged view of area C in FIG. 6A.
Figure 6C:
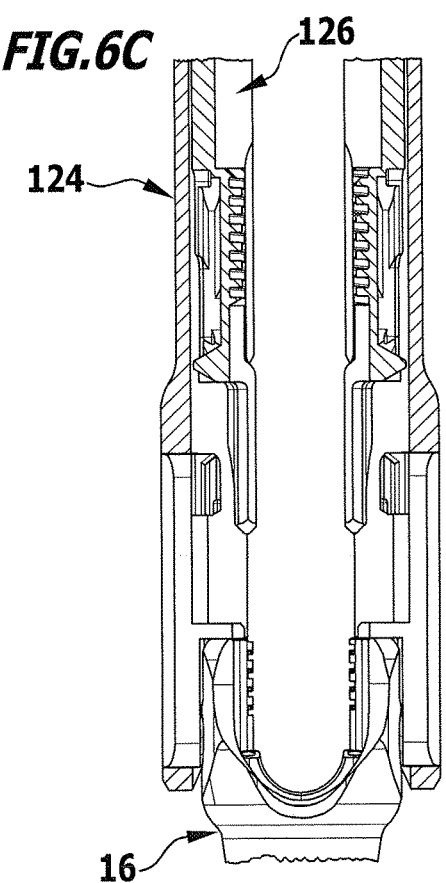
FIG. 6C shows an enlarged view of area D in FIG. 6A.
Figure 7A:
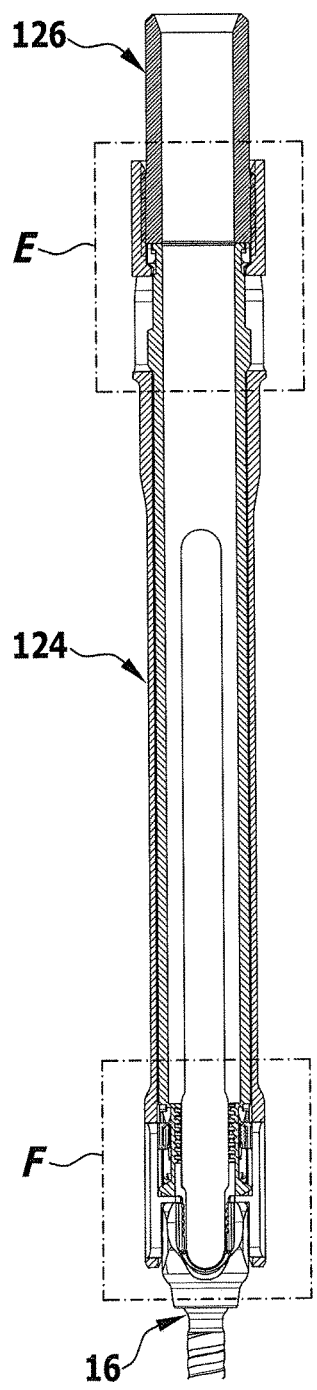
FIG. 7A shows a view in analogy with FIG. 6A, in which the inner sleeve is coupled to the fastening element.
Figure 7B:
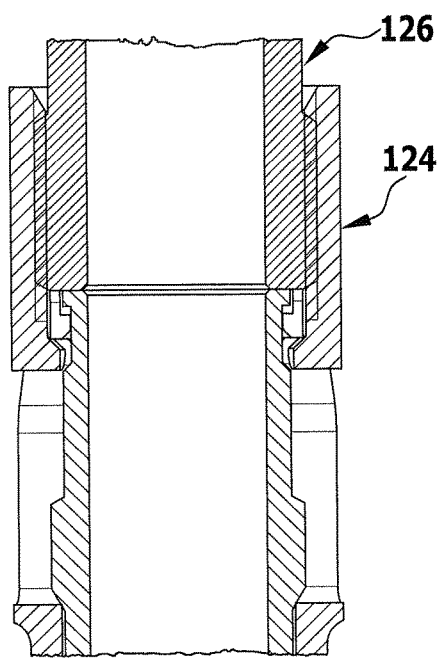
FIG. 7B shows an enlarged view of area E in FIG. 7A.
Figure 7C:
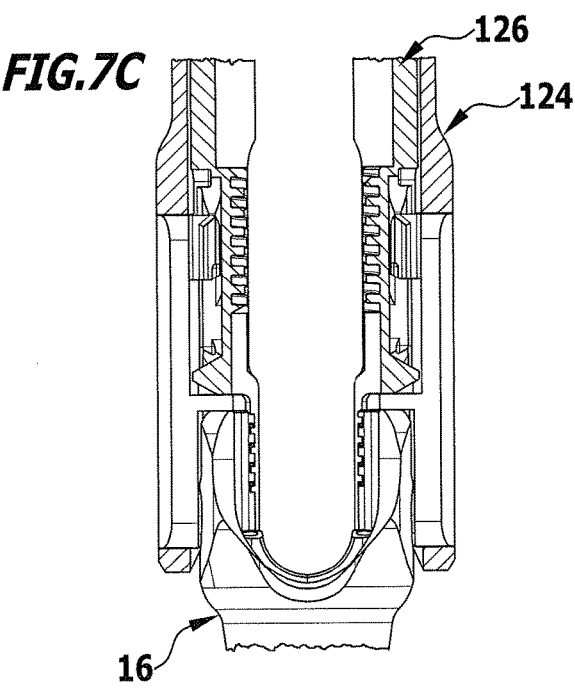
FIG. 7C shows an enlarged view of area F in FIG. 7A.
Figure 7D:
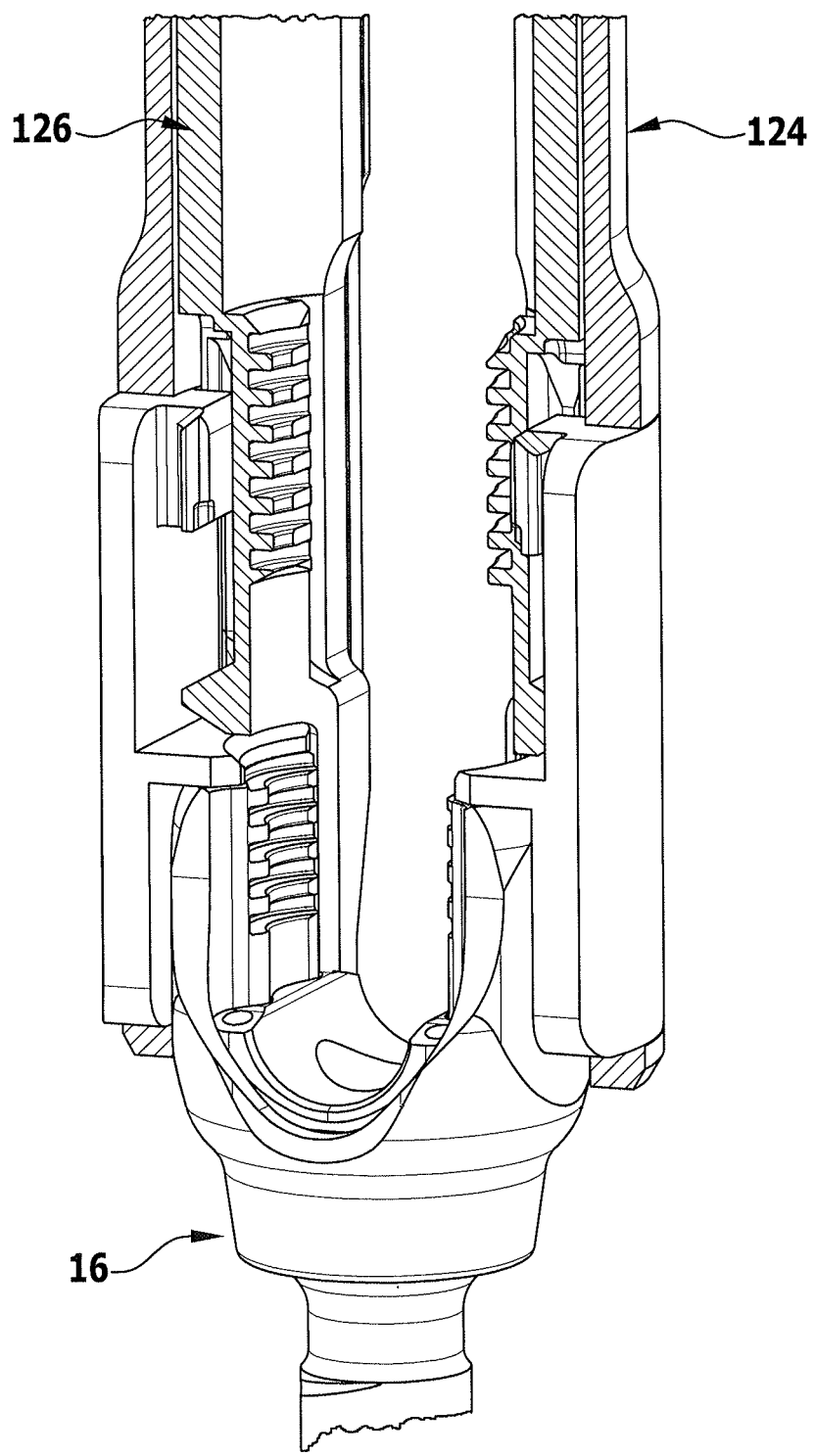
FIG. 7D shows a perspective view of area F in FIG. 7A.
Figure 8:
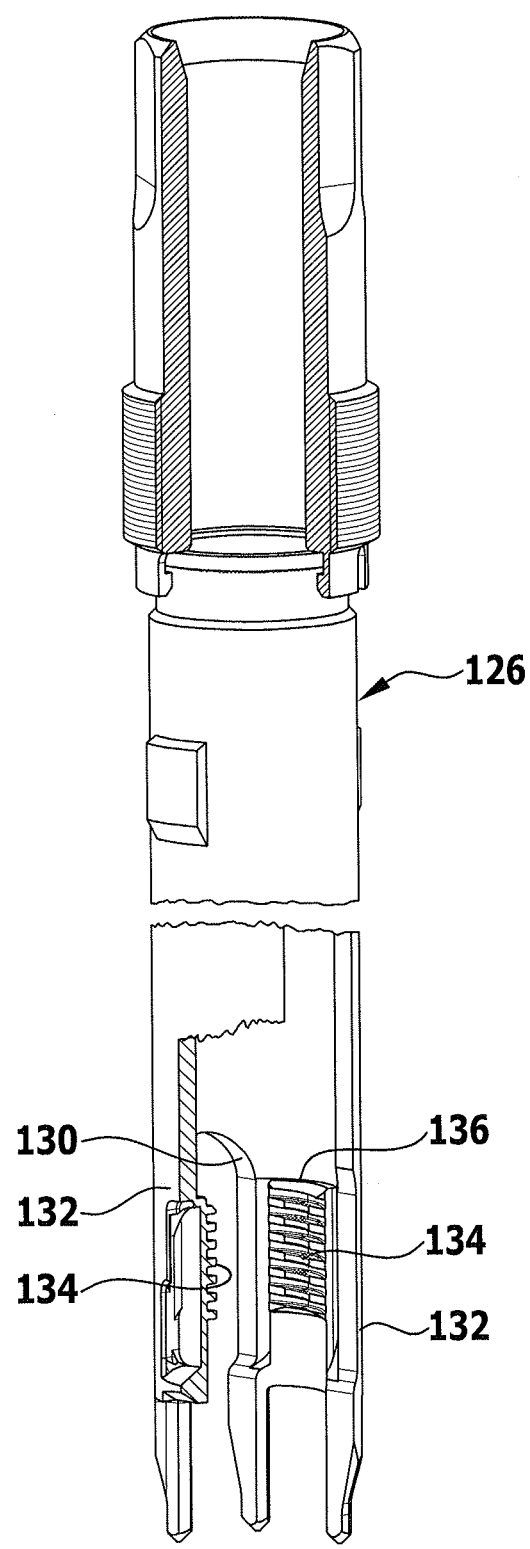
FIG. 8 shows a partially sectional view of the inner sleeve.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a surgical fastening element for a spinal column stabilization system comprising at least two fastening elements and at least one connecting element, said surgical fastening element comprising a fastening section, a holding section with a connecting element receptacle, and a fixing element fixable on the holding section for fixing the connecting element in the connecting element receptacle, wherein the fixing element carries a holding down element for holding the connecting element down in the connecting element receptacle.

The present invention further relates to a spinal column stabilization system comprising at least two surgical fastening elements and at least one connecting element, at least one of the at least two surgical fastening elements comprising a fastening section, a holding section with a connecting element receptacle, and a fixing element fixable on the holding section for fixing the connecting element in the connecting element receptacle, wherein the fixing element carries a holding down element for holding the connecting element down in the connecting element receptacle.

Constructing the fixing element of the surgical fastening element such that when it is introduced, it can simultaneously also press the connecting element into the connecting element receptacle and hold it therein, makes it possible to completely eliminate the hitherto separate operating step, namely that of pressing the connecting element into the connecting element receptacle and holding it therein. In accordance with the invention, the connecting element can already be pressed into the connecting element receptacle while introducing the fixing element. Owing to elimination of the operating step, the total duration of the surgery can be shortened and, in addition, the operation simplified. Furthermore, it may, in particular, be expedient if, in a connected position in which the fixing element and the holding down element are coupled or the fixing element carries the holding down element formed separately from it, a distal end of the holding down element projects beyond a distal end of the fixing element. The holding down element can thus press the connecting element into the connecting element receptacle, namely, in particular, without the fixing element, in particular, a distal fixing element section thereof, being in engagement with an internal thread of the holding section.

A particularly simple construction of the fastening element is achievable, in particular, by the fixing element being of sleeve-shaped or substantially sleeve-shaped construction and comprising a fixing element wall concentrically surrounding a longitudinal axis of the fixing element. In particular, this makes it possible to directly access a distal end of the fixing element, for example, through the fixing element, with a tool, in order to fix it on the holding section.

The fixing element expediently comprises a stop acting in the distal direction for the holding down element. In this way, movement of the holding down element relative to the fixing element can be limited in the proximal direction.

A particularly simple constructional design is achieved by the stop having a stop surface facing in the distal direction, against which the holding down element lies, in particular, in the connected position.

The fixing element is preferably constructed in the form of a fixing screw, which comprises an external thread starting from a distal end of the fixing screw and extending in the proximal direction, the external thread being constructed so as to correspond to an internal thread formed on the holding section. In particular, this configuration makes it possible to screw the fixing element into the internal thread of the holding section. The connecting element can thus be fixed in a simple and secure way to the connecting element receptacle.

Furthermore, it may be advantageous for the fixing element to have a predetermined break-off point which separates a distal fixing element section and a proximal fixing element section. This makes the fixing element as a whole easy to handle, with only part thereof having to ultimately remain on the holding section, in order to fix the connecting element there immovably.

The configuration of the fastening element is made particularly simple by the predetermined break-off point being formed by a recess extending circumferentially or substantially circumferentially in relation to the longitudinal axis and formed in the fixing element wall. In particular, the recess can be a wedge-shaped ring groove.

Manufacture of the fastening element is made particularly simple by the circumferential recess being formed so as to face away from the longitudinal axis. It is, for example, then possible for it to be formed in a last step of manufacture of the fixing element.

It is advantageous for the distal fixing element section to comprise a distal external thread section and for the proximal fixing element section to comprise a proximal external thread section. This configuration makes it possible to screw both the distal fixing element section and the proximal fixing element section jointly and/or separately, in each case, to corresponding internal thread sections on instruments and/or the holding section.

The fixing element preferably comprises a head which forms or includes the stop. The stop can thus be formed in a particularly simple way.

It is expedient for the head to have an outer diameter which is larger than an outer diameter of a shaft adjoining the head on the distal side. In this way, the stop can be realized particularly easily.

In particular, for positioning and mounting of the holding down element on the fixing element, it is advantageous for a thread-free shaft section to adjoin the head on the distal side, and for the external thread to adjoin the thread-free shaft section on the distal side.

For handling the fastening element, it is expedient for the holding down element to be rotatably mounted on the fixing element. For example, the holding down element can thus maintain its position or rotational position relative to the holding section and the fixing element can be simultaneously screwed in the axial direction.

Furthermore, it is advantageous for the holding down element to be held on the fixing element so as to be immovable or substantially immovable in the axial direction. With a movement of the fixing element in the direction towards the holding section, the holding down element can thus simultaneously press the connecting element into the connecting element receptacle and hold it therein.

The fastening element is particularly easy to manufacture when the holding down element is of sleeve-shaped or substantially sleeve-shaped construction. In particular, it can thus surround the fixing element, preferably on the distal side of the head, if the fixing element has such a head. In particular, an outer diameter of the holding down element can be adapted to an outer diameter of the head so that the head has a maximum outer diameter of a fixing unit formed by the fixing element and the holding down element.

It is expedient for the holding down element to comprise, in relation to a longitudinal axis, two diametrically opposed recesses. This makes it possible, for example, for the external thread of the fixing element to interact in the area of the recesses with an internal thread of an implantation instrument or with the internal thread of the holding section.

Construction of the holding down element is made particularly simple by the recesses being constructed in the form of slits starting from a distal end of the holding down element and extending in the proximal direction. Furthermore, such a configuration makes it possible to pivot the remaining lugs on the holding down element away from the longitudinal axis and towards the longitudinal axis.

In order to mount the holding down element in a defined and secure way on the fixing element, it is expedient for the holding down element to comprise a holding ring which carries two diametrically opposed holding down projections protruding in the distal direction. For example, the holding ring of the holding down element can be constructed so as to be closed in itself and, in particular, pushed over the fixing element from the distal side so that on the proximal side it strikes the stop which, in particular, may be formed on the head of the fixing element.

The holding ring preferably forms a proximal end of the holding down element. In particular, distal ends of the holding down projections can thus be brought into engagement with the connecting element to be positioned in the connecting element receptacle.

In accordance with a further preferred embodiment of the invention, it may be provided that the holding down projections are separated from each other by the two diametrically opposed recesses. As previously mentioned, with their distal ends the holding down projections can thus swivel out and/or spring out in the direction towards the longitudinal axis and/or away from the longitudinal axis, if the configuration and choice of the material from which the holding down element is formed are appropriate.

In order to have as large a contact surface as possible of the holding down element when lying against a connecting element, in particular, when the latter is of bar-shaped construction with round cross section, it is advantageous for distal ends of the holding down projections to be concavely curved facing in the distal direction.

To optimize a positioning of the holding down element on the fixing element, in particular, also a position of the holding down projections in the circumferential direction, it is advantageous for the holding down projections to carry guide projections facing in the circumferential direction and protruding at the side. These, therefore, engage around the fixing element somewhat further than the holding down projections themselves.

To improve insertion of the fixing element and, in particular, alignment thereof in the circumferential direction, it is expedient for the guide projections to have inclined slide surfaces facing in the distal direction. In this way, when inserting the fixing element carrying the holding down element, the holding down element can easily align itself automatically during the insertion into that rotational position which is necessary in order for a distal end of the holding down element to be able to enter into contact with the connecting element.

In a connected position in which the holding down element is coupled to the fixing element, it is advantageous for a proximal end of the holding ring to lie against the stop. If, for example, the fixing element is moved in the distal direction by an insertion tool, in particular, a screwdriver, engaging its head, the holding down element is then simultaneously moved along with it in the distal direction.

In order to achieve as compact a construction as possible, it is expedient for an outer diameter of the holding ring to correspond or correspond substantially to an outer diameter of the head.

In accordance with a further preferred embodiment of the invention, a locking connection can be provided for releasably connecting the fixing element and the holding down element in a connected position.

A particularly simple design of the fastening element can be achieved, in particular, by the locking connection comprising at least one locking projection and at least one locking recess interacting with the locking projection. In principle, the locking recess can be provided both on the holding down element and on the fixing element. The corresponding locking projection should then be provided on the respective other element.

It is expedient for the at least one locking projection to be formed by a ring projection on the holding down element facing in the direction towards the longitudinal axis. If the holding down element has two above-described, diametrically opposed slits, the ring projection is, consequently, also divided into two sections extending in the circumferential direction, which are then arranged or formed, in each case, on the holding down projections.

In order to make it easier for the at least one locking projection to be brought into engagement with the at least one locking recess, it is advantageous for the at least one locking projection to be arranged on the holding down element in the area of the holding down projections. In particular, such a configuration makes it possible for the at least one locking projection to be moved both in a direction towards the longitudinal axis and in a direction away from the longitudinal axis as a result of movement of the holding down projections.

The at least one locking recess is expediently formed on the fixing element between the head and the proximal external thread section. It is thus possible in a simple way for the at least one locking projection to engage this locking recess. In addition, it is easy for such a locking recess to be manufactured, in particular, by formation of a thread-free section between the external thread and a head of the fixing element.

To enable axial positioning of the holding down element on the fixing element to be achieved in a simple way, it is advantageous for the at least one locking projection to lie against or strike the proximal end of the proximal external thread section on the proximal side in the connected position. In particular, if a holding ring of the holding down element simultaneously lies against the stop of the fixing element, the holding down element is mounted on the fixing element so as to be axially secured against relative movement in relation to the fixing element.

To enable the fixing element to be brought in a desired manner into engagement with the holding section, it is expedient for the distal fixing element section to comprise a distal tool element receptacle which is open facing in the proximal direction. The distal tool element receptacle can be brought into engagement with a tool provided therefor, and the distal fixing element section brought into engagement with the holding section in such a way that the connecting element can be fixed in a defined way on the fastening element by means of the fixing element. The tool element receptacle can be of polygonal cross section, for example, it can be of hexagonal cross section. Tool element receptacles in the form of multiple inner rounded surfaces or of two, three or more bores formed on an inner wall surface of the distal fixing element section so as to overlap therewith are also conceivable.

The distal tool element receptacle preferably extends substantially over a length of the distal fixing element section in the axial direction. Essentially the entire available length of the distal fixing element section can, therefore, be used to be brought into engagement with an insertion tool.

Furthermore, it is advantageous for the proximal fixing element section to comprise a proximal tool element receptacle which is open facing in the proximal direction. For example, before severing the predetermined break-off point, with an insertion tool which can be brought into engagement with the proximal tool element receptacle, the fixing element can thus be moved in the distal direction and up to the holding section and, if required, brought into engagement therewith.

The proximal tool element receptacle preferably extends over a length of the fixing element, which corresponds to a length or substantially to a length of the head in the axial direction. In this way, a secure engagement of an insertion tool, for example, a screwdriver, with the proximal tool element receptacle can be ensured.

In particular, the proximal tool element receptacle can have a polygonal, in particular, quadrangular or hexagonal, cross section, or it may also be in the form of multiple inner rounded surfaces or be formed by making corresponding bores which overlap with an inner wall of the fixing element in this area.

A distal end of the fixing element is preferably closed. It, therefore, simultaneously forms a distal stop for an insertion tool, for example, a screw-in tool, to bring the distal fixing element section into engagement with the holding section and fix it thereon, for example, by screwing.

Furthermore, it may be advantageous for the distal end of the fixing element to be provided with at least one through-opening. The number of through-openings preferably corresponds to the number of recesses provided in an inner wall of the fixing element for formation of multiple inner rounded surfaces or the distal tool element receptacle.

To increase a stability of the fastening element, it is advantageous for the fixing element to be of integral construction. For example, it may be produced from a biocompatible metal which is suitable for absorbing the holding forces required to fix the connecting element.

The holding down element is preferably of integral construction. It can thus be, for example, easily manufactured, in particular, by injection molding from a steam-sterilizable plastic material such as, for example, polyetheretherketone (PEEK).

Furthermore, it may be advantageous for the fixing element and the holding down element to be formed from different materials. In particular, the two elements may be formed from materials which are particularly well-suited for the respective purpose, for example, the holding down element from a relatively soft material which cannot damage the connecting element during the holding down, for example, a sterilizable, biocompatible plastic material. In contrast to the holding down element, the fixing element may be produced from, for example, a biocompatible metal, in particular, titanium or a titanium alloy.

In accordance with a further preferred embodiment of the invention, it is advantageous for at least one of the surgical fastening elements of the spinal column stabilization system to be in the form of one the above-described, advantageous embodiments of surgical fastening elements. The spinal column stabilization system as a whole then has the advantages stated above.

In accordance with a further preferred embodiment of the spinal column stabilization system in accordance with the invention, it may be provided that it comprises a guide sleeve which is adapted to be temporarily coupled to the holding section and has an internal thread which corresponds to the external thread of the fixing element. For example, the guide sleeve may be formed as part of an insertion instrumentation included in the spinal column stabilization system. Owing to the internal thread on the guide sleeve, it is, for example, possible to screw the fixing element to the guide sleeve in order to thus define its position in the axial direction.

It is expedient for the guide sleeve to comprise a stop facing in the proximal direction for the head and/or the holding ring of the fixing element. In this way, it is possible to move the fixing element, in particular, its proximal fixing element section only as far as the stop facing in the proximal direction on the guide sleeve. The fixing element can thus be brought into engagement in a defined manner with the guide sleeve and clamped to it, so that in a next step, in particular, the distal fixing element section can be separated from the proximal fixing element section by destroying the predetermined break-off point and can preferably be brought into engagement with the internal thread on the holding section without force, in order to fix the connecting element in the connecting element receptacle.

To enable the distal fixing element section to be brought into engagement with the internal thread of the holding section without force, it is advantageous, in an assembly position in which the guide sleeve is coupled to the holding section, and the fixing element strikes the stop of the guide sleeve facing in the proximal direction, for the distal fixing element section to protrude on the distal side beyond the internal thread of the guide sleeve. The distal fixing element section can thus be separated from the proximal fixing element section by destroying the predetermined break-off point and without the application of force can be moved further in the distal direction and connected to the holding section.

Furthermore, it may be expedient, in the assembly position, for the distal fixing element section to be disengaged from the internal thread on the holding section. The distal fixing element section can thus be separated from the proximal fixing element section and brought into engagement with the internal thread on the holding section without force.

FIG. 1 shows diagrammatically a spinal column stabilization system denoted in its entirety by reference numeral 10, with which two or more adjacent vertebrae 12 of a spinal column 14 can be stabilized in their position relative to one another. The spinal column stabilization system 10 comprises a plurality of fastening elements 16 in the form of bone or pedicle screws 18, which have a fastening section 20 and a holding section 22.

The holding section 22 has a connecting element receptacle 24 for receiving a connecting element 26 and is formed on a head 28 of the pedicle screw 18. The head 28 is fork-shaped and, in relation to a longitudinal axis 30 of the fastening element 16, has diametrically opposed holding sections 32, which are provided with an internal thread 34.

The fastening section 20 is preferably in the form of a shaft 38 provided with a bone thread 36 so that the fastening element 16 can be screwed into the vertebra 12, in particular, into a pedicle thereof. Alternatively, the fastening section 20 may also be in the form of a bone hook or bone nail.

The fastening section 20 and the holding section 22 may optionally be of integral construction or, as in the embodiments shown in the Figures, be movable relative to each other, for example, pivotable about a joint center defined by a ball-and-socket joint formed between the fastening section 20 and the holding section 22. The pedicle screw 18 is, therefore, in particular, in the form of a polyaxial screw.

Figure 9C:
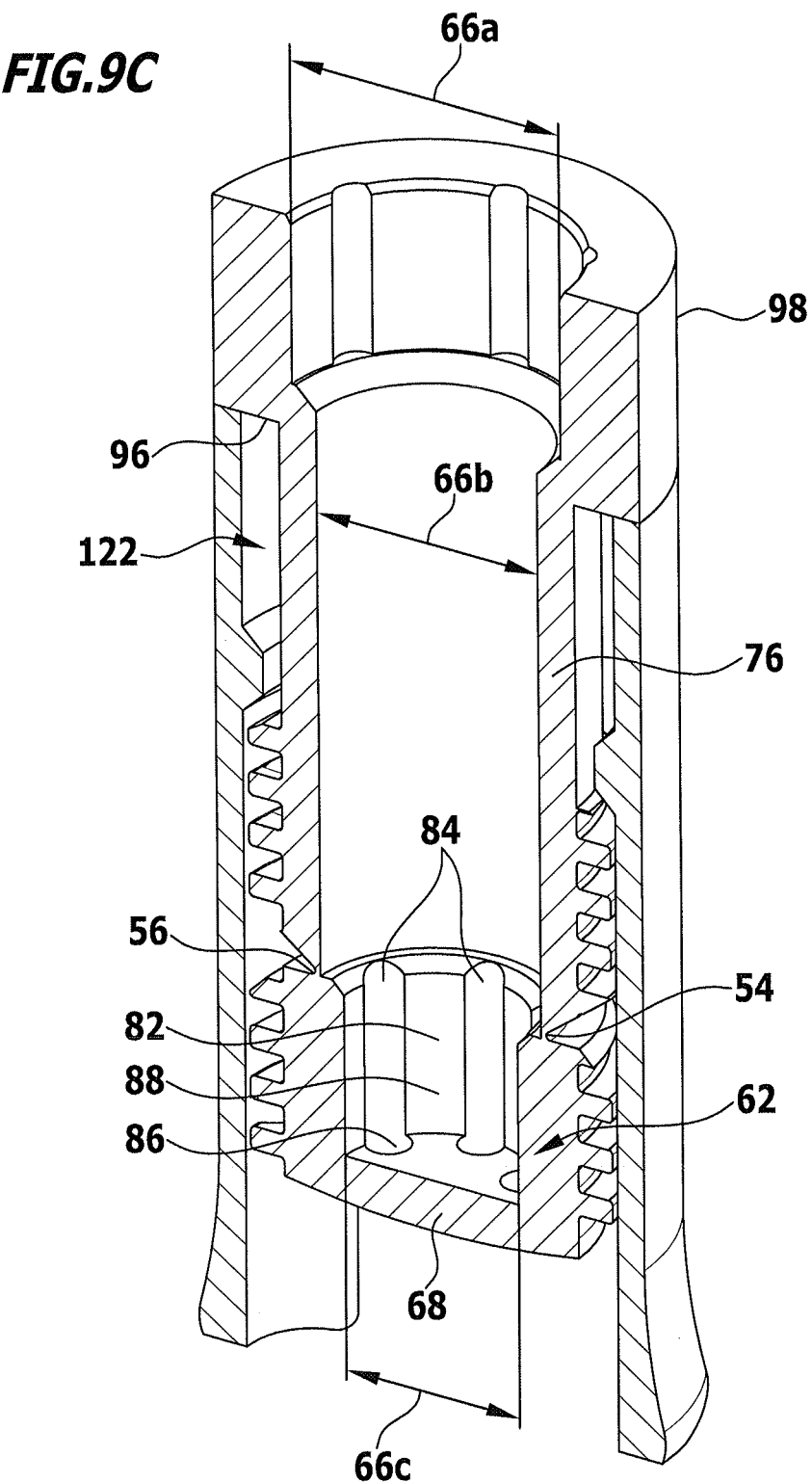
FIG. 9C shows a sectional view taken along line 9C-9C in FIG. 9B.

A fixing element 42, for example, in the form of the fixing screw 44 shown in FIG. 9A, serves to fix the connecting element 26, which may be in the form of a connecting rod 40 or a plate-shaped element. In a connected position, as shown diagrammatically in FIGS. 9B and 9C, the fixing screw 44 is connected or coupled to a holding down element to press and/or hold down the connecting element 26. In other words, it can also be said that the fixing element 42 carries the holding down element 46. The holding down element 46 is preferably mounted on the fixing element 42 so as to be rotatable, but axially immovable.

The construction of the fixing element 42 and the holding down element 46 will be explained in more detail below in conjunction with FIGS. 9A to 9C.

The fixing screw 44 has a cylindrical head 48 having connected thereto on the distal side a thread-free shaft section 50 of reduced diameter. Connected to the shaft section 50 on the distal side is an external thread 52, which is divided by a recess 56 forming a predetermined break-off point 54 into a proximal external thread section 58 and a distal external thread section 60. The recess 56 is in the form a ring groove, which surrounds the fixing element 42 on an outer side in the form of a ring, is preferably wedge-shaped and open facing away from the fixing element 42. The fixing element 42 is divided up by the predetermined break-off point 54 into a distal fixing element section 42 and a proximal fixing element section 64. All in all, the fixing element 42 is of integral construction and is preferably made of a biocompatible metal, for example, titanium or a titanium alloy.

The fixing element is hollow on the inside. All in all, it is therefore, essentially sleeve-shaped. An inner diameter of the fixing element 42 is reduced in its interior in two steps. In the area of the head 48, an inner diameter 66a is somewhat larger than an inner diameter 66b in the remaining part of the proximal fixing element section 64. An inner diameter 66c in the area of the distal fixing element section 62 is somewhat smaller again than the inner diameter 66b. The distal fixing element section 62 is closed on the distal side by a bottom 68 extending transversely to a longitudinal axis 70 of the fixing element 42.

A proximal tool element receptacle 72 open facing in the proximal direction is formed in the area of the head 48, namely by a total of six bores 74 which are aligned parallel to the longitudinal axis 70 and are partially formed in a hollow-cylindrical sleeve wall 76 of the fixing element 42 in the area of the head 48. Altogether, multiple inner rounded surfaces 78 are thus formed, which can be brought into engagement with a corresponding screw-in tool 80.

Figure 11A:
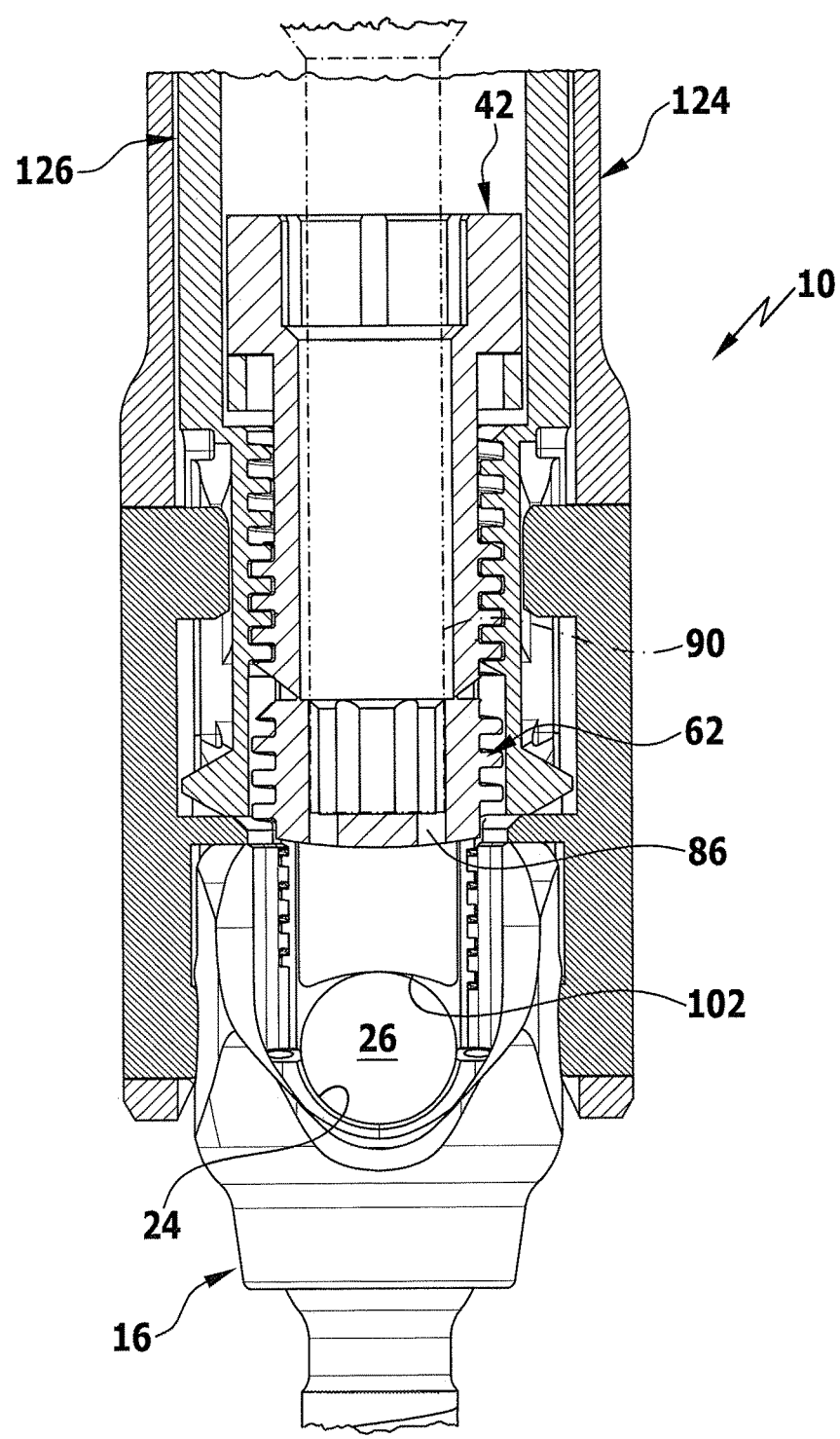
FIG. 11A shows a sectional view of the arrangement in FIG. 10B before severing the predetermined break-off point.
Figure 11B:
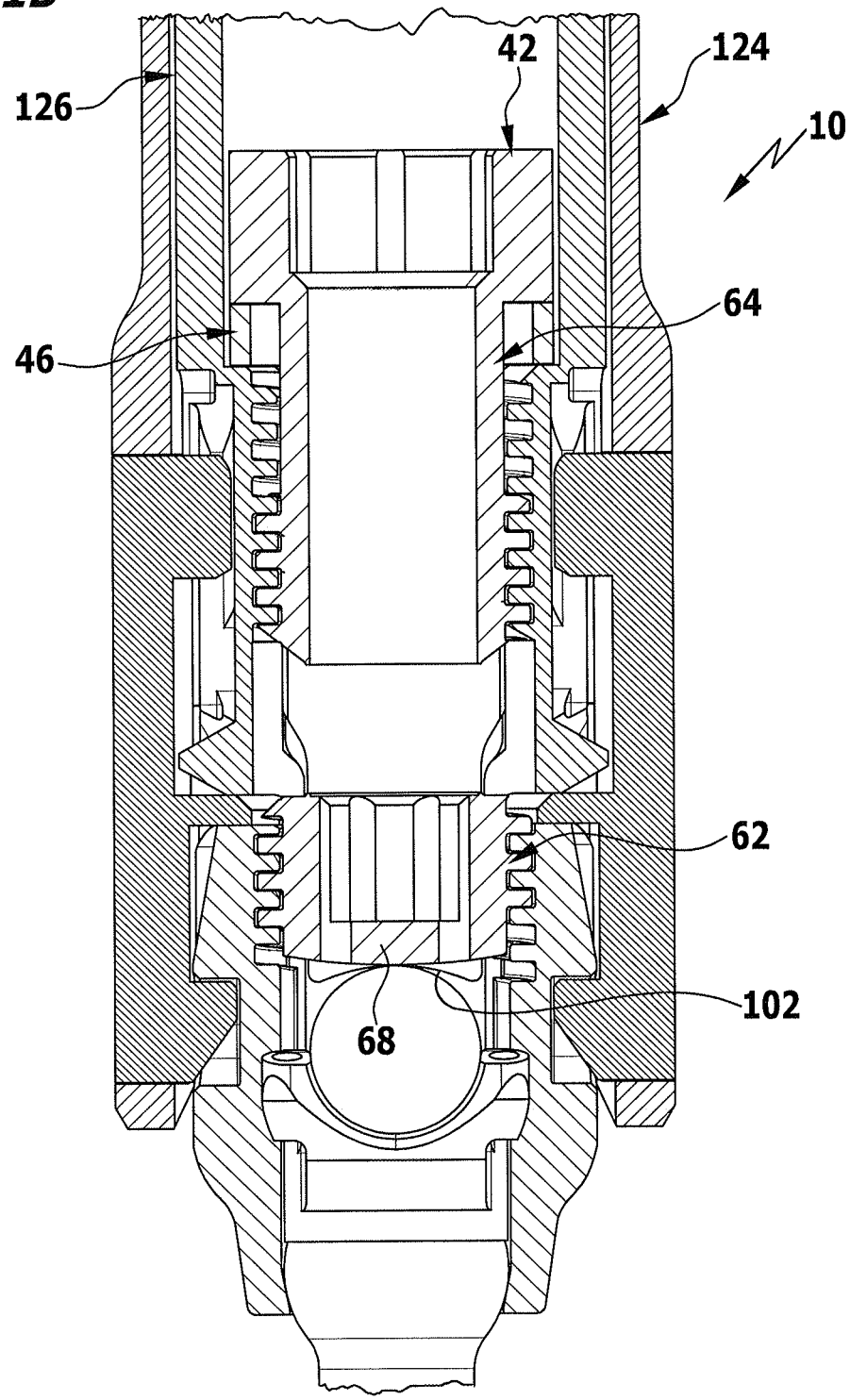
FIG. 11B shows a view similar to FIG. 11A after screwing the distal fixing element section into the internal thread of the holding section to fix the connecting element in the connecting element receptacle.

A distal tool element receptacle 82 formed essentially in analogy is formed in the interior of the distal fixing element section 62 by producing a total of six bores 84 which are aligned parallel to the longitudinal axis 70 and partially engage the sleeve wall 76 in the area of the distal fixing element section 62. Optionally, the bores 84, as shown in FIG. 9C, can also penetrate the bottom 68 and thus form through-openings 86 thereof. Altogether, the distal fixing element section 62, therefore, also has multiple inner rounded surfaces 88 which define the distal tool element receptacle 82. The tool element receptacle 82 can be brought into engagement with a correspondingly constructed screw-in tool 90, as shown diagrammatically in FIG. 11A.

The holding down element 46 is essentially sleeve-shaped and has a holding ring 94 closed in itself at its proximal end 92. In the connected position, the end 92 lies against a ring-shaped stop surface 96, facing in the distal direction, of the head 48 forming a stop 98. Extending in the distal direction from the holding ring 94 are two holding down projections 100, diametrically opposed in relation to the longitudinal axis 70, whose distal ends 102, in the connected position, protrude on the distal side beyond the bottom 68. The ends 102 are concavely curved facing in the distal direction and may optionally be adapted to a curvature of the element 26. An outer diameter of the holding ring 94 corresponds to an outer diameter of the head 48 and so an essentially cylindrical entire assembly consisting of the fixing element 42 and the holding down element 46, as shown diagrammatically in FIG. 9B, is formed in the connected position.

The holding down projections 100 are separated by slits 104 forming recesses 103 which, in relation to the longitudinal axis 70, are diametrically opposed. Formed at the sides of the holding down projections 100 are guide projections 106 which project in the circumferential direction and face each other. The guide projections 106 define inclined slide surfaces 108 facing in the distal or substantially in the distal direction. The guide projections 106 are spaced somewhat from the holding ring 94 so that indentations 110 open in the circumferential direction are formed.

Formed on the holding down projections 100 are locking projections 112 which protrude from an inner side 114 of the holding down element 46 and face in the direction towards the longitudinal axis 70. If the slits 104 were not present, the two locking projections 112 would be formed by a ring projection. The locking projections 112 are arranged somewhat to the distal side of the indentations 110 on the holding down projections 100. Facing in the distal direction, the locking projections 112 are slanted and, therefore, also have slide surfaces 116.

An outer diameter of the holding down element 46 increases slightly somewhat to the distal side of the guide projections 106 so that a slightly conical outer surface section 118 is formed towards the respective end 102.

The thread-free shaft section 50 forms for the locking projection 112 a locking recess 120 so that, all in all, a locking connection 122 is formed between the fixing element 42 and the holding down element 46. In the connected position, the locking projection 112 locks in the locking recess 120 when the holding down element 46 with the holding ring 94 is pushed beyond the external thread 52 and the shaft section 50 and strikes the head 48.

The holding down element 46 is preferably formed from a steam-sterilizable plastic material so that when the holding down element 46 and the fixing element 42 are united, the holding down projections 100 can swivel away somewhat from the longitudinal axis 70 and swivel back again resiliently in the direction towards the longitudinal axis 70 when the locking projection 112 enters the locking recess 120.

The implantation of the spinal column stabilization system 10 will be explained below diagrammatically in conjunction with FIGS. 1 to 11B.

In a first step, the fastening elements 16 are screwed in the required number into the vertebrae 12. To enable insertion of the connecting element 26 and subsequently the fixing element 42 into the holding sections 22, in a next step a guide sleeve 124 is coupled in a known manner by locking to the holding section 22. This is shown diagrammatically in FIGS. 4B and 4C.

After coupling of the guide sleeve 124 to the fastening element 16, in a next step an inner sleeve 126 serving to guide instruments is introduced from the proximal side into the guide sleeve 124. The inner sleeve 126 has at its distal end four rod-shaped projections 128 facing in the distal direction, which can be brought into engagement with both the holding section 22 and the guide sleeve 124. The introduction of the inner sleeve 126 into the guide sleeve 124 is shown diagrammatically in FIGS. 5A to 7D.

Alternatively to the two steps described above, an operating surgeon can also have an assistant reach him a unit consisting of guide sleeve 124 and inner sleeve 126 inserted therein, which he couples by locking to the holding section 22.

Starting from its distal end, the inner sleeve 126 is provided with two window-like indentations 130 which, in relation to the longitudinal axis 30, are diametrically opposed. There are, therefore, formed between these indentations 130 two coupling projections 132 which, are also diametrically opposed, in relation to the longitudinal axis 30, and face in the distal direction. The coupling projections 132 are provided with an internal thread 134 which is of the same dimensions as the internal thread 34. Both the internal thread 34 and the internal thread 134 are formed so as to correspond to the external thread 52.

Adjoining the internal thread 134 at the proximal side is a stop surface 136 facing in the proximal direction, whose function will be explained below.

In a next step, the connecting element 26 with a holding instrument 138 coupled thereto can be introduced through the indentations 130 into the connecting element receptacles 24 of the fastening elements 16, as shown diagrammatically in FIG. 1.

Unlike in spinal column stabilizations systems available on the market, it is now not necessary to press the connecting element 26 into the connecting element receptacle 24 with a further instrument. In the spinal column stabilization system 10, this function is assumed by the fixing element 42 carrying the holding down element 46.

Figure 10A:
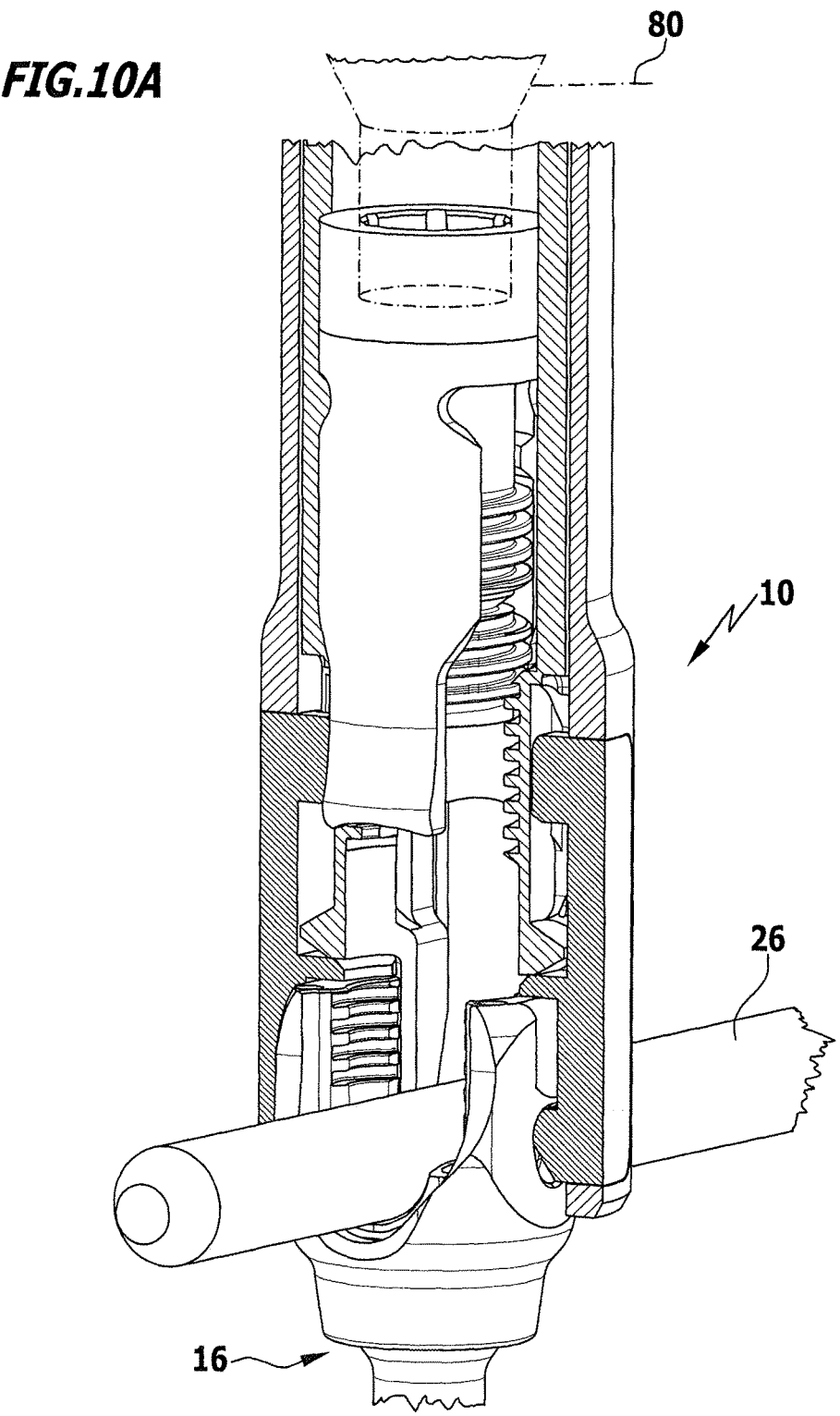
FIG. 10A shows a diagrammatic, partially sectional view taken when screwing in the fixing element with the holding down element through the inner sleeve.
Figure 10B:
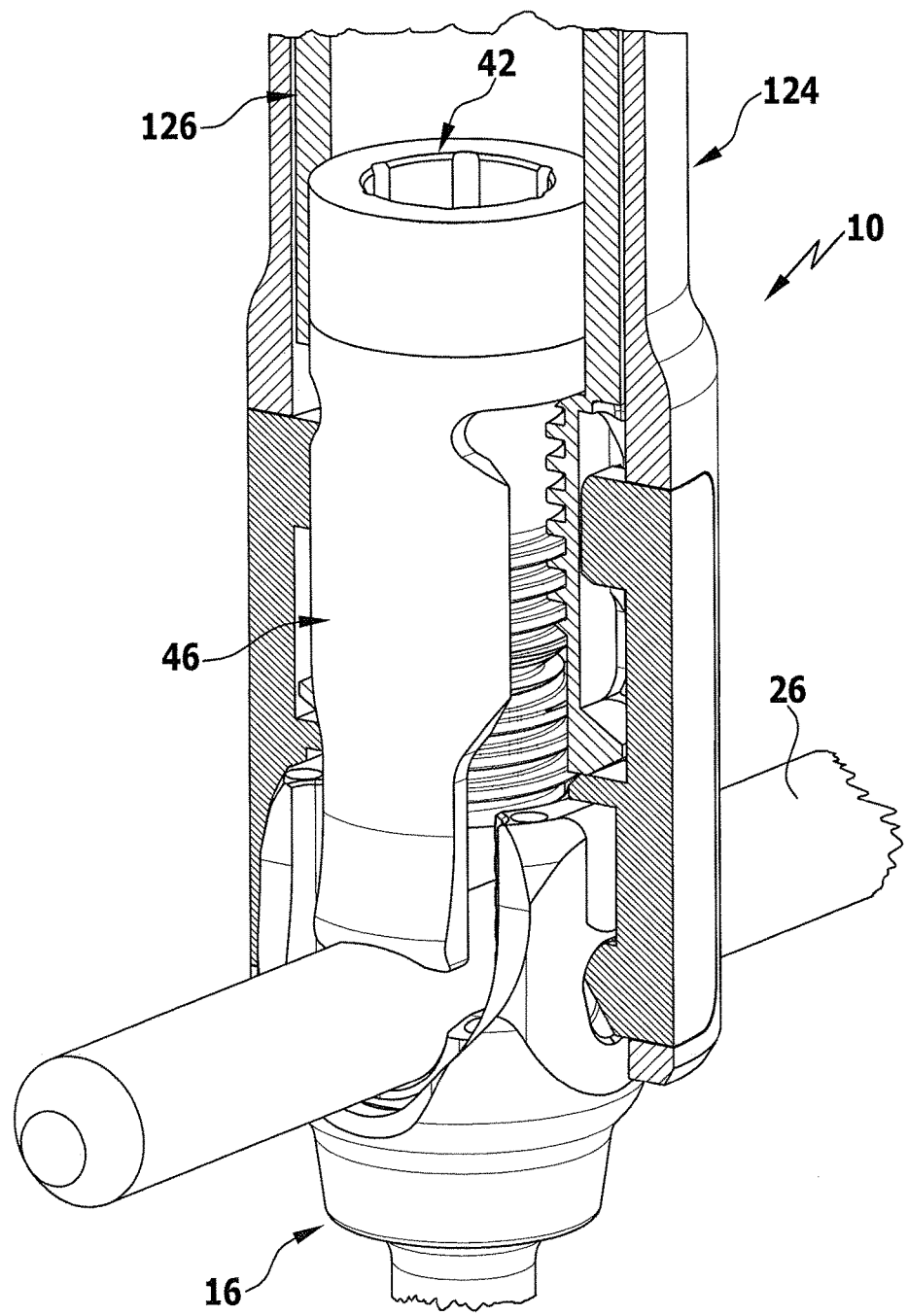
FIG. 10B shows a partially sectional view similar to FIG. 10A in the assembly position in which the holding ring of the holding down element strikes a stop of the inner sleeve facing in the proximal direction, and the holding down element presses the connecting element into the connecting element receptacle of the holding section.

As shown in FIG. 10A, in a next step, with the screw-in tool 80, which engages the proximal tool element receptacle 72, the fixing element 42 is screwed in the distal direction to the internal thread 134 of the inner sleeve 126, namely until the holding ring 94 strikes the stop surface 136, as shown diagrammatically in FIG. 10B. During the screwing-in, the ends 102 of the holding down projections 100 enter into contact with the connecting element 26 and press it, during the further screwing-in of the fixing element 42, into the connecting element receptacle 24. With the holding down element 46, the fixing element 42 holds the connecting element 26 in the connecting element receptacle 24, as is evident again from a different perspective in section in FIG. 11A. From this Figure it is also clear that in this assembly position, in which the holding ring 94 strikes the stop surface 136, the distal fixing element section 62 protrudes at the distal side beyond the internal thread 134, and is, therefore, not in engagement therewith.

To finally fix the connecting element 26 held by the holding down element 46 in the connecting element receptacle 24 on the holding section 22, the screw-in tool 80 is withdrawn and the screw-in tool 90 introduced and with its distal end brought into engagement with the distal tool element receptacle 82. Owing to the proximal fixing element section 64 being coupled to the inner sleeve 126 by being screwed in, the predetermined break-off point 54 can be destroyed by applying a corresponding torque and the distal fixing element section 62 irreversibly separated from the proximal fixing element section 64. The distal fixing element section 62 is, therefore, free and can be moved further in the distal direction independently of the proximal fixing element section 64 and brought into engagement with the internal thread 34 and screwed into it until the bottom 68 strikes the connecting element 26 and the connecting element 26 is thus finally held clamped in the connecting element receptacle 24.

In the described manner, all of the required connecting elements 26 are fixed with the fixing elements 42 on the holding sections 22 of the fastening elements 16.

Finally, the proximal fixing element section 64 with the holding down element 46 arranged thereon is screwed out in the proximal direction with the screw-in tool 80, the inner sleeve 126 is pulled in the proximal direction out of the guide sleeve 124, and the guide sleeve 124 is uncoupled from the holding section 22. Alternatively, the unit consisting of guide sleeve 124 and inner sleeve 126, as a whole, can also be removed in one step. The spinal column stabilization system 10 is now fixed as desired to the vertebrae 12.

In particular, the described spinal column stabilization system 10 can, therefore, do without extensions protruding in the proximal direction from the holding section 22, as provided in known systems, in which case the extensions have to be removed, for example, by being broken off, after fixing of the fixing element 42 on the holding section 22. Furthermore, in the described spinal column stabilization system 10, the provision of a rod press-in instrument, for example, in the form of a further press-down sleeve engaging around the outside of the guide sleeve 124 is rendered superfluous. This would have the further disadvantage that a skin incision for minimally invasive access for implantation of the spinal column stabilization system 10 would have to be enlarged somewhat. This disadvantage is eliminated by the proposed spinal column stabilization system 10.

Figure 12:
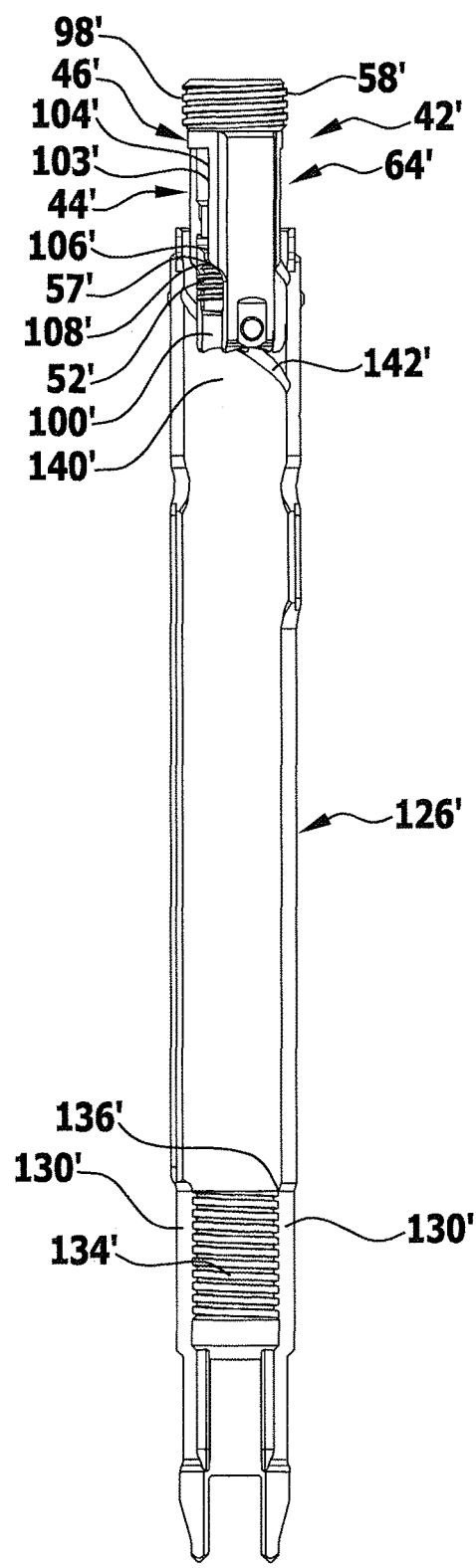
FIG. 12 shows a longitudinal sectional view of a further embodiment of an inner sleeve when inserting a correspondingly constructed fixing element.
Figure 13:
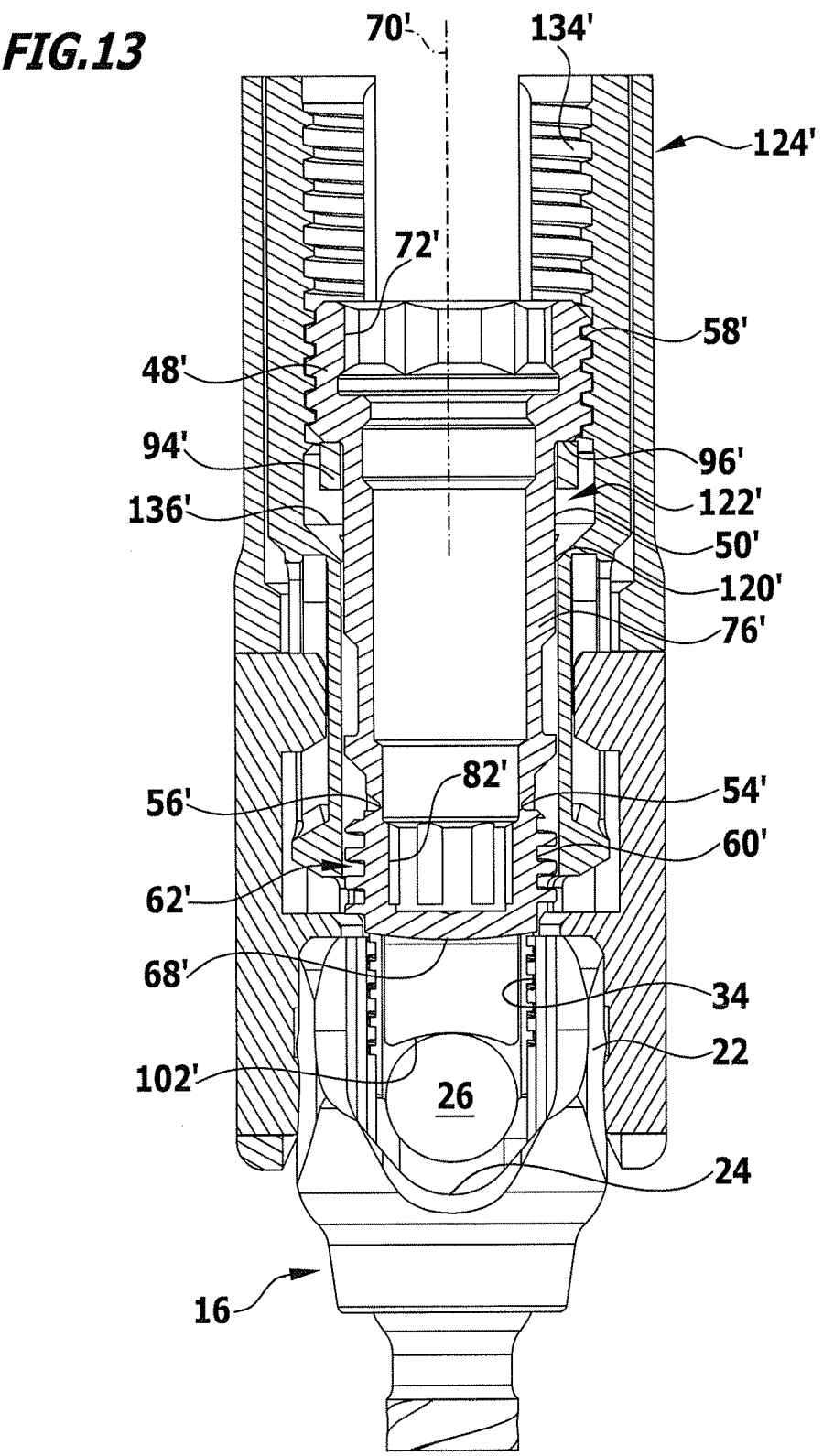
FIG. 13 shows a sectional view similar to the arrangement in FIG. 10B of a further embodiment of a fixing element with a correspondingly constructed inner sleeve before severing the predetermined break-off point.

Alternative embodiments of an inner sleeve 126' and of a fixing element 42' interacting with the inner sleeve 126' are shown diagrammatically in FIGS. 12 and 13. In their construction and in their functioning, they correspond substantially to the inner sleeve 126 and the fixing element 42.

The difference between the inner sleeve 126' and the inner sleeve 126 is essentially that the internal thread 134' is arranged somewhat further in the proximal direction on the inner sleeve 126' than the internal thread 134 on the inner sleeve 126. The internal thread 134' is, therefore, arranged in the area in which the inner diameter of the inner sleeve 126' is widened somewhat. The internal thread 134' is thus arranged at the location where in the inner sleeve 126 the head of enlarged outer diameter in relation to the external thread 52 is arranged when the fixing element 42 is pushed forward to the maximum extent in the distal direction, as shown diagrammatically in FIG. 11A. In contrast thereto, the internal thread 134' is now arranged exactly where the head 48' is seated. It interacts with the external thread of the proximal external thread section 58' which is formed on the head 48' of the fixing element 42'. The fixing element 42', therefore, has two external thread sections which are spatially clearly separated from each other, namely the distal external thread section 60' on the distal fixing element section 62' and the proximal external thread section 58' on the proximal fixing element section 64'. The proximal and distal external thread sections 58' and 60', therefore, also differ in their diameter, the distal external thread section 60' being of somewhat smaller outer diameter.

The inner sleeve 126' has a further difference from the inner sleeve 126. Starting from its proximal end, a helical groove 142' is formed in an inner wall surface 140' of the inner sleeve 126'. A corresponding projection of a holding down projection 100' of the fixing element 42' engages the helical groove 142' so that on inserting the fixing element 42' into the inner sleeve 126', the holding down projections 100' are aligned with the slit-shaped indentations 130' in such a way that they can engage these.

The way in which the fixing element 42' functions corresponds essentially to the functioning of the fixing element 42. In an analogous manner, as described in conjunction with FIGS. 10A, 10B, 11A and 11B, with the screw-in tool 80 engaging the proximal fixing element receptacle 72', the fixing element 42' is screwed in the distal direction to the internal thread 134' of the inner sleeve 126', namely until the distal ends 102' of the holding down projections 100' strike the connecting element 26. When the fixing element 42' is screwed in further, the ends 102' of the holding down projections 100' press the connecting element 26 into the connecting element receptacle 24. With the holding down element 46', the fixing element 42' holds the connecting element 26 in the connecting element receptacle 24, as shown diagrammatically in FIG. 13. It is also clearly evident from this Figure that in this assembly position in which the distal ends 102' of the holding down projections 100' strike the connecting element 26, the distal fixing element section 62' is not yet in engagement with the internal thread 34.

In order to finally fix the connecting element 26 held by the holding down element 46' in the connecting element receptacle 24 on the holding section 22, the screw-in tool 80 is withdrawn and the screw-in tool 90 inserted and with its distal end brought into engagement with the distal tool element receptacle 82'. Owing to the proximal fixing element section 64' being coupled to the inner sleeve 126' by being screwed in, the predetermined break-off point 54' can be destroyed by applying a corresponding torque and the distal fixing element section 62' irreversibly separated from the proximal fixing element section 64'. The distal fixing element section 62' is, therefore, free and can be moved further in the distal direction independently of the proximal fixing element section 64' and brought into engagement with the internal thread 34 and screwed into it until the bottom 68' strikes the connecting element 26 and the connecting element 26 is thus finally held clamped in the connecting element receptacle 24.

In other respects, the spinal column stabilization system 10 functions in an analogous way with the inner sleeve 126' and the fixing element 42' as described above.

Optionally, the functions of the screw-in tool 80 and the screw-in tool 90 may also be united in a single instrument which, in particular, may be of multipart construction.

The invention claimed is:

1. A surgical fastening element for a spinal column stabilization system that includes at least two fastening elements and at least one connecting element, said surgical fastening element comprising:
   a fastening section;
   a holding section with a connecting element receptacle; and
   a fixing element fixable on the holding section for fixing the connecting element in the connecting element receptacle,
   wherein the fixing element carries a holding down element for holding the connecting element down in the connecting element receptacle,
   wherein the fixing element comprises a pre-determined break-off point which separates a proximal fixing element section and a distal fixing element section,
   wherein the holding down element is rotatably mounted on the proximal fixing element section;
   wherein the holding down element is held on the fixing element so as to be immovable or substantially immovable relative to the fixing element in the axial direction, and
   wherein the holding down element bears against the proximal fixing element section.

2. A surgical fastening element in accordance with claim 1, wherein the fixing element comprises at least one of:

A) a sleeve-shaped or substantially sleeve-shaped construction having a fixing element wall that concentrically surrounds a longitudinal axis of the fixing element; and B) a stop acting in the distal direction for the holding down element.

3. A surgical fastening element in accordance with claim 2, wherein the fixing element comprises a head which forms or includes the stop.

4. A surgical fastening element in accordance with claim 3, comprising at least one of:
   A) an outer diameter of the head which is larger than an outer diameter of a shaft adjoining the head on the distal side; and
   B) a thread-free shaft section adjoining the head on the distal side, the external thread adjoining the thread-free shaft section on the distal side.

5. A surgical fastening element in accordance with claim 1, wherein the fixing element comprises:
   a construction in the form of a fixing screw, which comprises an external thread starting from a distal end of the fixing screw and extending in the proximal direction, and the external thread is constructed so as to correspond to an internal thread formed on the holding section.

6. A surgical fastening element in accordance with claim 1, wherein the distal fixing element section comprises a distal external thread section, and wherein the proximal fixing element section comprises a proximal external thread section.

7. A surgical fastening element in accordance with claim 1, wherein the holding down element comprises at least one of the following features:
   the holding down element is of sleeve-shaped or substantially sleeve-shaped construction; and
   the holding down element comprises, in relation to a longitudinal axis, two diametrically opposed recesses.

8. A surgical fastening element in accordance with claim 1, wherein the holding down element comprises a holding ring which carries two diametrically opposed holding down projections protruding in the distal direction.

9. A surgical fastening element in accordance with claim 8 comprising at least one of the following features:
   A) the holding ring forms a proximal end of the holding down element;
   B) the holding down projections are separated from each other by the two diametrically opposed recesses;
   C) distal ends of the holding down projections are concavely curved facing in the distal direction; and
   D) the holding down projections carry guide projections facing in the circumferential direction and protruding at the side.

10. A surgical fastening element in accordance with claim 8 comprising at least one of the following features:
    A) a proximal end of the holding ring lies against a stop in a connected position in which the holding down element is coupled to the fixing element; and
    B) an outer diameter of the holding ring corresponds or corresponds substantially to an outer diameter of a head of the fixing element.

11. A surgical fastening element in accordance with claim 1, comprising a locking connection for releasably connecting the fixing element and the holding down element in a connected position.

12. A surgical fastening element in accordance with claim 11, wherein the locking connection comprises at least one locking projection and at least one locking recess interacting with the locking projection.

13. A surgical fastening element in accordance with claim 12, wherein the at least one locking projection is at least one of:
    A) formed by a ring projection on the holding down element facing in the direction towards the longitudinal axis; and
    B) arranged on the holding down element in the area of the holding down projections.

14. A surgical fastening element in accordance with claim 1, wherein the distal fixing element section comprises a distal tool element receptacle which is open facing in the proximal direction.

15. A surgical fastening element in accordance with claim 1, wherein the proximal fixing element section comprises a proximal tool element receptacle which is open facing in the proximal direction.

16. A surgical fastening element in accordance with claim 1, wherein a distal end of the fixing element is closed.

17. A surgical fastening element in accordance with claim 1 comprising at least one of the following features:
    A) the fixing element is of integral construction;
    B) the holding down element is of integral construction; and
    C) the fixing element and the holding down element are formed from different materials.

18. A spinal column stabilization system comprising:
    at least two surgical fastening elements; and
    at least one connecting element,
    at least one of the at least two surgical fastening elements comprising a fastening section, a holding section with a connecting element receptacle, and a fixing element fixable on the holding section for fixing the connecting element in the connecting element receptacle,
    wherein the fixing element comprises a proximal fixing element section and a distal fixing element section,
    wherein the fixing element carries a holding down element for holding the connecting element down in the connecting element receptacle, the holding down element bearing against the proximal fixing element section,
    wherein the holding down element is rotatably mounted on the proximal fixing element section; and
    wherein the holding down element is held on the fixing element so as to be immovable or substantially immovable relative to the fixing element in the axial direction.

19. A spinal column stabilization system in accordance with claim 18, comprising a guide sleeve, which is adapted to be temporarily coupled to the holding section and has an internal thread which corresponds to the external thread of the fixing element.

20. A spinal column stabilization system in accordance with claim 19, wherein the guide sleeve comprises a stop facing in the proximal direction for a head and/or a holding ring of the fixing element.

* * * * *